United States Patent
Sleijfer et al.

(10) Patent No.: US 10,555,926 B2
(45) Date of Patent: Feb. 11, 2020

(54) USE OF CABAZITAXEL IN THE TREATMENT OF PROSTATE CANCER

(71) Applicant: Erasmus University Medical Center Rotterdam, Rotterdam (NL)

(72) Inventors: Stefan Sleijfer, Rotterdam (NL); Wendy Onstenk, Rotterdam (NL); Anita Maria Sieuwerts, Rotterdam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 0 days.

(21) Appl. No.: 15/551,708

(22) PCT Filed: Feb. 17, 2016

(86) PCT No.: PCT/NL2016/050111
§ 371 (c)(1),
(2) Date: Aug. 17, 2017

(87) PCT Pub. No.: WO2016/133387
PCT Pub. Date: Aug. 25, 2016

(65) Prior Publication Data
US 2018/0064678 A1 Mar. 8, 2018

(30) Foreign Application Priority Data
Feb. 17, 2015 (EP) .................................. 15155470

(51) Int. Cl.
A61K 31/337 (2006.01)
A61K 31/573 (2006.01)
C12Q 1/6886 (2018.01)
G01N 33/574 (2006.01)

(52) U.S. Cl.
CPC .......... *A61K 31/337* (2013.01); *A61K 31/573* (2013.01); *C12Q 1/6886* (2013.01); *G01N 33/57434* (2013.01); *C12Q 2600/156* (2013.01); *G01N 2333/4742* (2013.01); *G01N 2333/70589* (2013.01); *G01N 2333/723* (2013.01)

(58) Field of Classification Search
CPC ............... A61K 31/337; A61K 31/573; G01N 33/57434; G01N 2333/723; G01N 2333/70589; G01N 2333/4742; C12Q 1/6886; C12Q 2600/156
See application file for complete search history.

(56) References Cited

U.S. PATENT DOCUMENTS 7,241,907 B2 * 7/2007 Didier .................... A61K 31/58
549/510
2012/0301425 A1 * 11/2012 Gupta .................. A61K 31/164
424/85.1

FOREIGN PATENT DOCUMENTS

WO 2014047285 A1 3/2014

OTHER PUBLICATIONS

Onstenk et al, European Urology, 68, 939-945. (Year: 2015).*
Antonarakis et al, JAMA Oncol., 1(5):582-591 (Year: 2015).*
Antonarakis, Emmanuel S., et al. "AR-V7 and resistance to enzalutamide and abiraterone in prostate cancer." New England Journal of Medicine, vol. 371, No. 11, pp. 1028-1038, Sep. 2014.
De Bono, Johann Sebastian, et al. "Prednisone plus cabazitaxel or mitoxantrone for metastatic castration-resistant prostate cancer progressing after docetaxel treatment: a randomised open-label trial." The Lancet, vol. 376, No. 9747, pp. 1147-1154, Oct. 2010.
International Search Report and Written Opinion dated Jun. 20, 2016 in PCT Application No. PCT/NL2016/050111 (12 pages).
Janssen, The CellSearch (R) System for the Enumeration of Circulating Tumor Cells. Retrieved from URL: https://www.cellsearchctc.com/sites/default/files/docs/cellsearch-brochure.pdf Jan. 1, 2013.
Qu, Yuanyuan, et al. "Constitutively active AR-V7 plays an essential role in the development and progression of castration-resistant prostate cancer." Scientific Reports, vol. 5, paper 7654, Jan. 2015.
Veridex LLC, Cellsearch (R) Epithelial Cell Kit—Instructions for Use, REF 7900000. Retrieved from URL: https://www.cellsearchruo.com/sites/default/files/CELLSEARCH-Epithelial-Cell-Kit-PI-631-50-007-1.pdf Mar. 7, 2013.

* cited by examiner

*Primary Examiner* — Sudhakar Katakam
(74) *Attorney, Agent, or Firm* — Dentons US LLP

(57) ABSTRACT

The present invention relates to cabazitaxel for use in a method for treating an AR-V7-positive patient suffering from prostate cancer comprising determining the AR-V7-status in said patient and administering cabazitaxel. The invention also relates to a method of identifying patients with prostate cancer, eligible for treatment with cabazitaxel comprising testing a biological sample from the patient for the presence of AR-V7 circulating tumor cells, wherein the patient is eligible for treatment with said cabazitaxel if circulating tumor cells in said sample test positive for AR-V7. The invention further relates to a kit of parts for determining the AR-V7-status in isolated tumor cells of a patient with prostate cancer.

19 Claims, 13 Drawing Sheets

Figure 4C (continued)

| date | 28-Jul-14 | 26-Nov-14 | 26-Nov-14 | 25-Aug-14 | 25-Aug-14 | 22-Sep-14 | 25-Aug-14 | 28-Jul-14 | 22-Sep-14 | 28-Jul-14 | 22-Sep-14 | 22-Sep-14 | 28-Jul-14 | 22-Sep-14 | 22-Sep-14 |
|---|---|---|---|---|---|---|---|---|---|---|---|---|---|---|---|
| Sample description | HBD | VCAP in HBD | VCAP in HBD | VCAP CellSearch enriched | VCAP | VCAP | VCAP | VCAP | VCAP | VCAP | VCAP | VCAP | VCAP | VCAP | VCAP |
| Input # cells in RT-qPCR | 0 | 2 | 10 | 10 | 40 | 40 | 80 | 90 | 100 | 250 | 250 | 250 | 125 | 65 | 15 |
| pre-amplified | no | no | no | yes | yes | yes | yes | yes | yes | yes | yes | no | no | no | no |
| WBC present | no | no | no | yes | no | no | no | no | no | no | no | no | no | no | no |
| dCq PPMK/CD45 | 6.16 | 6.47 | 5.81 | 3.67 | No Cq | No Cq | No Cq | No Cq | No Cq | No Cq | No Cq | No Cq | No Cq | No Cq | No Cq |
| Mean Cq 3 reference genes | 22.30 | 21.50 | 21.64 | 23.93 | 21.13 | 21.49 | 19.21 | 19.32 | 18.93 | 18.75 | 15.99 | 25.87 | 24.89 | 28.32 | 30.80 |
| Mean Cq 2 epithelial markers | No Cq | 25.70 | 23.68 | 24.17 | 19.92 | 19.99 | 17.82 | 17.94 | 17.38 | 14.97 | 14.68 | 24.64 | 23.06 | 26.71 | 29.55 |
| Cq AR-V7 | No Cq | 29.58 | 27.87 | 29.94 | 24.54 | 24.10 | 22.01 | 22.79 | 21.27 | 20.12 | 18.41 | 28.48 | 27.37 | 31.35 | 33.14 |

Figure 7

```
   1 gacactgaat tggaaggtg gaggattttg tttttttctt ttaagatctg ggcatctttt
  61 gaatctaccc ttcaagtatt aagagacaga ctgtgagcct agcagggcag atcttgtcca
 121 ccgtgtgtct tcttctgcac gagactttga ggctgtcaga gcgcttttg cgtggttgct
 181 cccgcaagtt tccttctctg gagcttcccg caggtgggca gctagctgca gcgactaccg
 241 catcatcaca gcctgttgaa ctcttctgag caagagaagg ggaggcgggg taagggaagt
 301 aggtggaaga ttcagccaag ctcaaggatg gaagtgcagt tagggctggg aagggtctac
 361 cctggccgc cgtccaagac ctaccgagga gctttccaga atctgttcca gagcgtgcgc
 421 gaagtgatcc agaacccggg ccccaggcac ccagaggccg cgagcgcagc acctcccggc
 481 gccagtttgc tgctgcagca gcagcagcag cagcagcagc agcagcagca gcagcagcag
 541 cagcagcagc agcagcagca gcagcagcag cagcagcagc aagagactag ccccaggcag
 601 cagcagcagc agcagggtga ggatggttct ccccaagccc atcgtagagg cccacaggc
 661 tacctggtcc tggatgagga acagcaacct tcacagccgc agtcggccct ggagtgccac
 721 cccgagagag gttcgtccc agagctgga gcggccgtgg ccgccagcaa ggggctgcg
 781 cagcagctgc cagcacctcc ggacgaggat gactcagctg cccccatcca cgttgtccctg
 841 ctgggcccca ctttccccgg cttaagcagc tgctccgctg accttaaaga catcctgagc
 901 gaggccagca ccatgcaact cctcagcaa cagcagcagg aagcagtatc cgaaggcagc
 961 agcagcggga gcgcgaggga ggcctcgggg gctcccactt cctccaagga caattactta
1021 ggggcacttt cgaccatttc tgacaacgcc aaggagttgt gtaaggcagt gtcggtgtcc
1081 atgggcctgg tgtggaggc gttggagcat ctgagtccag gggaacagct tgggggat
1141 tgcatgtacg cccactttt gggagttcca cccgctgtgc gtcccactcc ttgtgcccca
1201 ttggccgaat gcaaaggttc tctgctagac gacagcgcag gcaagagcac tgaagatact
1261 gctgagtatt cccctttcaa gggaggttac accaaagggc tagaaggcga gagcctaggc
1321 tgctctggca gcgtcagc agggagctcc gggacacttg aactgccgtc taccctgtct
1381 ctctacaagt ccggagcact ggacgaggca gctgcgtacc agagtcgcga ctactacaac
1441 tttccactgg ctctggccgg accgccgccc cctccgcgc ctccccatcc ccagctcgc
1501 atcaagctgg agaacccgct ggactacggc agcgcctggg cggctgcggc ggcgcagtgc
1561 cgctatgggg actggcgag cctgcatggc gcggtgcag cgggaccgg ttctgggtca
1621 ccctcagccg ccgcttcctc atcctggcac actctcttca cagccgaaga aggccagttg
1681 tatggaccgt gtggtggtgg tgggggtggt ggcgcggcg gcggcggcg cggcggcggc
1741 ggcggcggcg aggcgggagc tgtagccccc tacggctaca ctcggccccc tcagggctg
1801 gcgggcaggg aaagcgactt caccgcacct gatgtgtggt accctggcgg catggtgagc
1861 agagtgccct atcccagtcc cacttgtgtc aaaagcgaaa tgggccctg gatgtatagc
1921 tactccggac cttacgggga catgcgttg gagactgcca gggaccatgt tttgcccatt
1981 gactattact ttccaccca gaagacctgc ctgatctgtg gagatgaagc ttctggtgt
2041 cactatggag ctctcacatg tggaagctgc aaggtcttct tcaaaagagc cgctgaaggg
2101 aaacagaagt acctgtgcgc cagcagaaat gattgcacta ttgataaatt ccgaaggaaa
2161 aattgtccat cttgtcgtct tggaaatgt tatgaagcag ggatgactct gggagaaaaa
2221 ttccggttg gcaattgcaa gcatctcaaa atgaccagac cctgaagaaa ggctgacttg
2281 cctcattcaa aatgagggct ctagagggct ctagtggata gtctggagaa acctggctc
2341 tgaggcttag gagcttaggt ttttgctcct caacacagac ttgacgttg gggttgggg
2401 ctactctctt gattgctgac tcctccagc gggaccaata gtgttttcct acctcacagg
2461 gatgttgtga ggacgggctg tagaagtaat agtggttacc actcatgtag ttgtgagtat
2521 catgattatt gtttcctgta atgtggcttg gcattggcaa agtgctttt gattgttctt
2581 gatcacatat gatggggcc aggactgac tcagcggat gcagtgaagc tctgctcag
2641 tcgcttgctt ttcgtggtgt gctgccagga agaaactttg ctgatgggac tcaaggtgtc
2701 accttggaca agaagcaact gtgtctgtct gaggttcctg tggccatctt tatttgtgta
2761 ttaggcaatt cgtattccc ccttaggttc tagccttctg gatcccagcc agtgacctag
2821 atcttagcct caggccctgt cactgagctg aaggtagtag ctgatccaca gaagttcagt
2881 aaacaaggac cagatttctg cttctccagg agaagaagcc agccaaccc tctcttcaaa
2941 cacactgaga gactacagtc cgactttccc tcttcatctct agccttactg tagccacact
3001 ccttgattgc tctctcacat cacatgcttc tcttcatcag ttgtaagcct ctcattcttc
3061 tcccaagcca gactcaaata ttgtattgat gtcaaagaag aatcacttag agtttggaat
3121 atcttgttct ctctctgctc catagcttcc atattgacac cagtttcttt ctagtgggaga
3181 agtggagtct gtgaagccag ggaaacacac atgtgagagt cagaaggact ctccctgact
```

Figure 7 (continued)

```
3241 tgcctggggc ctgtctttcc cacttctcc agtctgtcta aacacacaca cacacacaca
3301 cacacacaca cacacacaca cacacgctct ctctctctct cccccccaa cacacacaca
3361 ctctctctct cacacacaca cacatacaca cacacttctt tctctttccc ctgactcagc
3421 aacattctgg agaaaagcca aggaaggact tcaggagggg agtttccccc ttctcagggc
3481 agaattttaa tctccagacc aacaagaagt tccctaatgt ggattgaaag gctaatgagg
3541 tttattttta actactttct atttgtttga atgttgcata tttctactag tgaaattttc
3601 cctaataaa gccattaata cacccaaaaa aaaaaaaaaa a
```

USE OF CABAZITAXEL IN THE TREATMENT OF PROSTATE CANCER

RELATED APPLICATIONS

The present application is a U.S. National Phase Application under 35 U.S.C. § 371 of International Application No. PCT/NL2016/050111, filed on Feb. 17, 2016, which claims priority to and the benefit of European Patent Application No. 15155470.6, filed on Feb. 17, 2015. All of the foregoing applications are hereby incorporated by reference in their entirety.

FIELD OF THE INVENTION

The present invention relates to a novel antitumoral use of cabazitaxel in the treatment of prostate cancer, which may be metastatic, especially for patients with castration-resistant prostate cancer. In particular, the present invention relates to the use of cabazitaxel in the treatment of patients with castration resistant metastatic prostate cancer, wherein said patients have a positive status for the androgen receptor splice variant V7.

BACKGROUND OF THE INVENTION

Prostate cancer affects a large proportion of the male population worldwide and is generally treated with therapies at curative intent (radical prostatectomy or radiation therapy) with or without androgen deprivation therapy when disease is localized or for cases with advanced disease not amendable for curative options with androgen deprivation therapy, immunotherapy, chemotherapy or radiopharmaceuticals.

First-line chemotherapy in castration resistant prostate cancer (CRPC) patients is docetaxel (sold under the brand name Taxotere®) in combination with prednisone and is associated with a survival benefit of 2.4 months. Docetaxel may be combined with other chemotherapies such as estramustine or platinum agents.

To date, docetaxel plus prednisone is considered the standard of care as first-line chemotherapy treatment for metastatic CRPC.

An important problem with all therapies is that the cancer may become resistant to the agents used, in particular to taxanes, which limits the possible treatment options. Recently, a novel therapeutic option for treating prostate cancer was provided, especially for patients with metastatic castration resistant prostate cancer (mCRPC) who have been previously treated with docetaxel based regimen. Abiraterone acetate and enzalutamide both act on androgen receptor (AR) signaling and improve overall survival (OS) in the pre- and post-docetaxel setting. Cabazitaxel (Jevtana®), the next-generation taxane, has been developed to overcome docetaxel resistance and blocks cell division through stabilization of microtubules. Like enzalutamide and abiraterone acetate, cabazitaxel lends OS benefit in docetaxel pre-treated mCRPC patients. Cabazitaxel is currently approved by the FDA as second-line treatment after docetaxel. A large number of clinical trials on cabazitaxel have been performed or are underway. All these trials emphasize that the critical issues are now how to optimally sequence treatment lines for mCRPC patients; how to best select patients for cabazitaxel; and, even more important, how to best individualize treatment. There is a need for biomarkers that can predict response/resistance of prostate tumours to new drugs, including cabazitaxel and new androgen receptor (AR)-targeted agents such as abiraterone acetate and enzalutamide.

Preclinical as well as clinical data indicate cross-resistance between abiraterone acetate, enzalutamide, and docetaxel. Inhibition of AR signaling seems to be the shared mechanism of action between the three agents responsible for this cross-resistance as microtubule stabilization by docetaxel next to inhibition of cell division also inhibits nuclear transport of AR. In contrast, patients pre-treated with abiraterone acetate, enzalutamide, and docetaxel still appear to benefit from cabazitaxel. Prior treatment thus seems to impact outcome to subsequent therapy, stressing the need for reliable predictive factors reflecting tumor characteristics in real time.

Circulating tumor cells (CTCs) from peripheral blood have attracted major attention over the past decade. A CTC count before and during treatment is a strong, independent prognostic factor for progression-free survival (PFS) and OS in mCRPC, and outperforms prostate specific antigen (PSA) measurements as an early treatment response marker. Potentially of even greater importance than CTC enumeration, is the characterization of CTCs. Recently, presence of the AR mRNA splice variant 7 (AR-V7), coding for a truncated and constitutively active AR, was assessed in CTCs of mCRPC patients starting enzalutamide or abiraterone acetate (Antonarakis et al. 2014. N Engl J Med. 371:1028-38). In the small cohort of patients investigated, none of the patients with AR-V7 transcripts in their CTCs responded to abiraterone acetate or enzalutamide, compared to 68% and 53%, respectively, of patients without AR-V7 (Antonarakis et al. 2014). Presence of AR-V7 was measured using reverse transcription quantitative polymerase chain reaction (RT-qPCR) on CTCs enriched by the AdnaTest (AdnaGen AG, Langenhagen, Germany), for which limited data concerning the validity in mCRPC exist. Abovementioned results strongly suggest that AR-V7-positive patients should not receive enzalutamide or abiraterone acetate. However, it remains to be elucidated whether cabazitaxel remains an effective treatment option for these patients.

SUMMARY OF THE INVENTION

The invention relates to a further medical indication of the antitumoral pharmaceutical therapeutic use of cabazitaxel of formula:

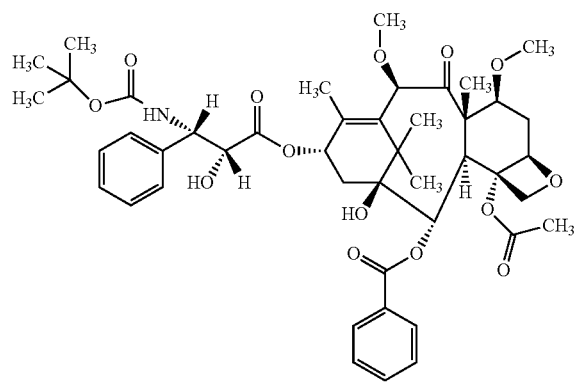 [SMILES: CO[C@H]1C(=O)[C@]2(C)[C@@H](OC)C[C@H]3OC[C@@]3(OC(C)=O)[C@H]2[C@H](OC(=O)c2ccccc2)[C@]2(O)C[C@H](OC(=O)[C@H](O)[C@@H](NC(=O)OC(C)(C)C)c3ccccc3)C(C)=C1C2(C)C]

In particular, the invention, in a first aspect, relates to cabazitaxel for use as a medicament in the treatment of a patient suffering from prostate cancer comprising determining the AR-V7-status in said patient and administering cabazitaxel in base form or in the form of an hydrate or a solvate, to said patient, in combination with a corticoid.

In another aspect, the present invention relates to a method for treating a patient suffering from prostate cancer, the method comprising the step of determining the AR-V7-status in a patient and administering to said patient cabazitaxel in base form or in the form of an hydrate or a solvate, in combination with a corticoid.

In another aspect, the present invention relates to the use of cabazitaxel in base form or in the form of an hydrate or a solvate in combination with a corticoid for the manufacture of a medicament for treating a patient suffering from prostate cancer, wherein said use comprises determining the AR-V7-status in said patient.

In preferred embodiments of the above aspects, the prostate cancer is metastatic castration-resistant prostate cancer (mCRPC). However, AR-V7 may also be detected in metastatic non castration resistant prostate cancer as well as localized castration or non-castration resistant prostate cancer.

In other preferred embodiments of the above aspects, the step of determining the AR-V7-status in said patient is performed on isolated tumor cells. In preferred embodiments, said isolated tumor cells are circulating tumor cells (CTCs).

In highly preferred embodiments of the above aspects, the step of determining the AR-V7-status in said patient is performed on isolated CTCs using the CELLSEARCH® Circulating Tumor Cell Test (CELLSEARCH® Circulating Tumor Cell Kit (Epithelial) Janssen Diagnostics, LLC).

In some preferred embodiments of the above-referenced aspects, the patient has been previously treated with a docetaxel-based regimen.

In some other preferred embodiments of the above aspects of the invention, the patient is resistant to docetaxel, and new AR-targeted agents, such as abiraterone acetate and/or enzalutamide, or the patient, when pretreated with docetaxel and/or new AR-targeted agents, has not yet become resistant to docetaxel and/or new AR-targeted agents. In such embodiments, cabazitaxel in base form or in the form of an hydrate or a solvate, in combination with a corticoid, is used as part of a second-line cytotoxic chemotherapy for the treatment of prostate cancer, preferably mCRPC.

Alternatively, in other preferred embodiments of the above aspects of this invention, the patient has not been pretreated with docetaxel and/or AR-targeted agents. In such embodiments, cabazitaxel in base form or in the form of an hydrate or a solvate, in combination with a corticoid, is used as part of a first-line cytotoxic chemotherapy for the treatment of prostate cancer, preferably mCRPC.

In the above-referred aspects of the invention, treating patients with prostate cancer preferably comprises administering an effective amount of the antitumoral agent cabazitaxel to said patient.

This antitumoral agent may be in the form of anhydrous base, a hydrate or a solvate, intended for treating prostate cancer, in particular patients who have been previously treated with a docetaxel-based regimen. This compound is preferably administered to a patient with metastatic disease which has become castration resistant. Cabazitaxel is preferably administered in combination with a corticoid chosen especially from prednisone and prednisolone. This corticoid is preferably administered at a daily dose of 10 mg orally.

In some aspects of the invention, cabazitaxel is administered in combination with prednisone for its use as a medicament in the treatment of patients with hormone-refractory prostate cancer who have been previously treated with docetaxel based regimen.

In some aspects of the invention, cabazitaxel is administered at a dose (defined for each administration) of between 20 and 25 mg/m$^2$. Cabazitaxel may be in the form of an acetone solvate. More particularly, the acetone solvate of cabazitaxel contains between 5% and 8% and preferably between 5% and 7% by weight of acetone.

In some aspects of the invention, cabazitaxel may be administered by intravenous infusion at a dose of between 15 and 25 mg/m$^2$, this administration cycle of the antitumour agent being repeated at an interval of 3 weeks between each cabazitaxel administration, which interval may be prolonged by 1 to 2 weeks depending on the tolerance to the preceding cabazitaxel administration.

In some embodiments, the effective amount of cabazitaxel produces at least one therapeutic effect selected from the group consisting of increase in overall survival, partial response, reduction in tumor size, reduction in metastasis, complete remission, partial remission, stable disease, or complete response.

The present invention also relates to a pharmaceutical composition that treats patients with prostate cancer comprising a clinically proven safe and effective amount of cabazitaxel.

Further embodiments of the invention comprise methods or using, treating, promoting, and providing cabazitaxel.

The present invention also provides a method of treating prostate cancer, preferably mCRPC, in a patient, comprising testing the AR-V7-status of circulating tumor cells in a biological sample from the patient and administering a therapeutically effective amount of cabazitaxel in base form or in the form of an hydrate or a solvate, in combination with a corticoid to the patient if the sample tests positive for AR-V7.

In a preferred embodiment, a method of treating prostate cancer, preferably mCRPC, in a patient according to the present invention, comprises:

(a) determining the AR-V7-status in isolated tumor cells, preferably isolated circulating tumor cells, in one of a blood, serum or urine sample obtained from the patient, said step of determining comprising:

magnetically separating said tumor cells from essentially all other cells in the sample using ferrofluid nanoparticles with antibodies that target epithelial cell adhesion, preferably anti-EpCAM antibodies loaded with ferrofluid nanoparticles, to provide an enriched tumor cells sample;

optionally enumerating said isolated tumor cells in said enriched tumor cells sample by staining said tumor cells in said sample with a nuclear DNA stain, preferably DAPI, and a cytokeratin monoclonal antibody specific to epithelial cells, preferably anti-cytokeratin 8/18/19, while optionally differentiating said dual stained tumor cells from stained leukocytes in said sample using a leukocyte-specific anti-CD45 monoclonal antibody stain, and determining the presence of androgen receptor mRNA splice variant 7 transcripts in tumor cells in said enriched tumor cells sample by reverse transcription quantitative polymerase chain reaction (RT-qPCR), whereby the presence of AR-V7 transcripts in said tumor cells indicates an AR-V7-positive status of said patient; and (b) treating the prostate cancer in the patient in case said patient has an AR-V7-positive status comprising administering to said patient a therapeutically effective amount of cabazitaxel in base form or in the form of an hydrate or a solvate, in combination with a corticoid, preferably prednisone or prednisolone.

The present invention also provides a method for treating an AR-V7-positive patient suffering from prostate cancer comprising administering cabazitaxel in base form or in the form of an hydrate or a solvate, to a AR-V7-positive patient in need thereof, optionally in combination with a corticoid.

The present invention also provides a method of identifying patients with prostate cancer, preferably mCRPC, eligible for treatment with cabazitaxel in base form or in the form of an hydrate or a solvate, in combination with a corticoid comprising testing a biological sample from the patient for the presence of AR-V7 circulating tumor cells, as described above, wherein the patient is eligible for treatment with said cabazitaxel if AR-V7 is present in said circulating tumor cells.

The present invention also relates to packages and articles of manufacture.

In particular, the present invention provides diagnostic kits for determining the AR-V7-status in isolated tumor cells, preferably isolated circulating tumor cells, in one of a blood, serum or urine sample obtained from a patient with prostate cancer, said kit comprising amplification primers for amplifying androgen receptor mRNA splice variant 7 transcripts in tumor cells by reverse transcription quantitative polymerase chain reaction (RT-qPCR), and further comprising ferrofluid nanoparticles with antibodies that target epithelial cell adhesion, preferably anti-EpCAM antibodies loaded with ferrofluid nanoparticles, for enriching tumor cells from essentially all other cells in the patient sample by magnetic separation, optionally in combination with instructions for determining the eligibility of the patient with prostate cancer to treatment with cabazitaxel based on the diagnostic test result results for the AR-V7-status obtained.

BRIEF DESCRIPTION OF THE DRAWINGS

FIG. 7. The nucleotide sequence of the AR-V7 mRNA encoding region, as provided by GenBank accession number FJ235916. The sequence of the AR-V7-specific CE3 region, starting at nucleotide 2216, is underlined. An in-frame stop codon at position 2263-2265 is indicated in bold.

DETAILED DESCRIPTION OF THE INVENTION

Definitions

Figure 1:
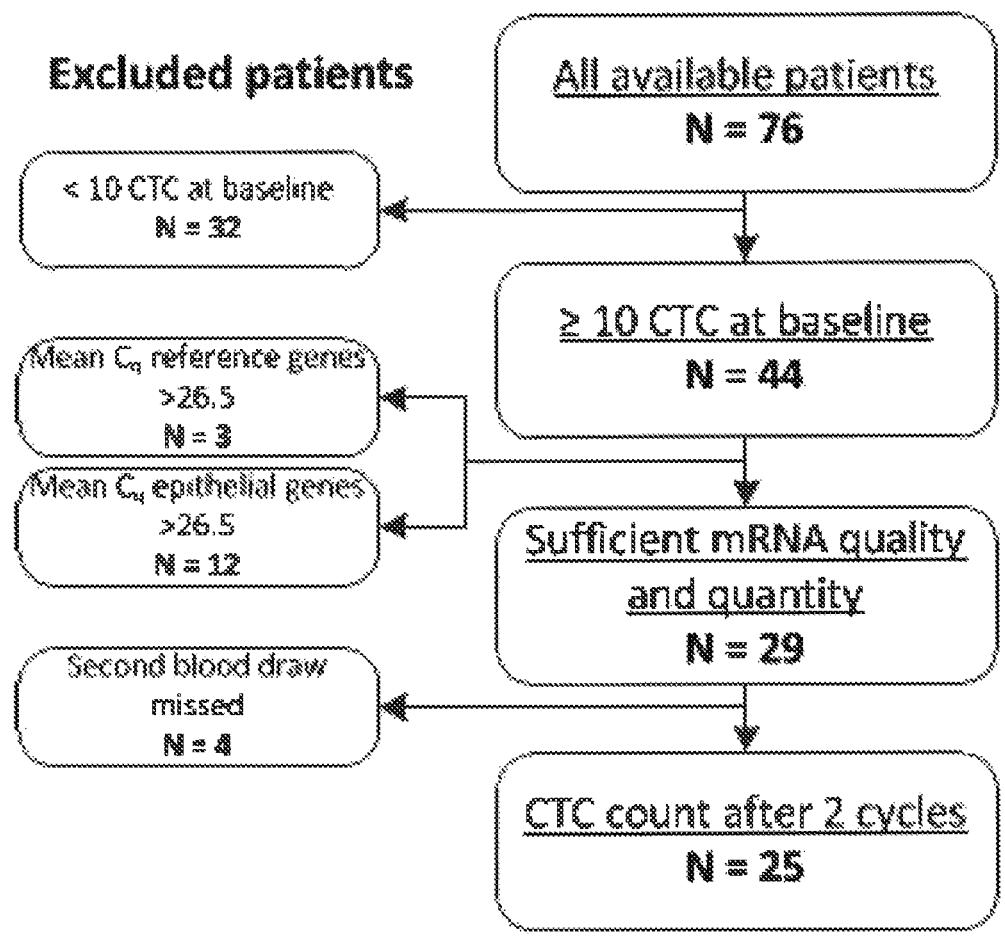
FIG. 1. Study flow chart showing the selection of patients for the analyses.

The term "effective amount", as used herein, means an amount of a pharmaceutical compound, such as cabazitaxel, that produces an effect on the cancer to be treated.

The term "clinically proven", as used herein, means clinical efficacy results that are sufficient to meet FDA approval standards.

The term "castration resistant prostate cancer", as used herein, is synonymous with hormone-refractory prostate cancer and refers to patients with prostate cancer who have failed to treatment aiming to reduce androgen levels to castration levels.

The term "patient", as used herein, includes both human and animals. In one embodiment, a patient is a human.

The term "androgen receptor" or "AR" refers to the androgen receptor protein as defined by its conserved amino acid coding sequence in an active or native structural conformation. Nucleic acid sequences encoding androgen receptors have been cloned and sequenced from numerous organisms. The GenBank® accession number for the human androgen receptor sequence is NM-000044.3 (PRI 11 May 2014). The androgen receptor (AR) is a hormone-activated transcription factor that regulates eukaryotic gene expression and affects proliferation and differentiation of target cells. The full length protein is cytoplasmic in the absence of hormone, but translocates to the nucleus upon binding of either testosterone or dihydrotestosterone. The androgen receptor is encoded by the X-chromosomal androgen receptor gene. The AR gene comprises 8 exons and 7 introns. Two AR isoforms are known, A and B, of which AR-B represents the full length receptor and AR-A represents a N-terminally truncated protein that lacks the first 187 amino acids due to in vitro proteolysis (Gregory et al., 2001. J Mol Endocrinol 27: 309-19). The prototype AR protein contains an NH2-terminal (N-terminal) domain (NTD), encoded by exon 1, which constitutes about 60% of the 110-kDa full-length protein and is the transcriptional regulatory region of the protein. The central DNA-binding domain (DBD) is encoded by exons 2 and 3, whereas exons 4 to 8 code for the COOH-terminal ligand-binding domain (LBD) (Hu et al., 2009. Cancer Res 69: 16-22).

The term "androgen receptor (AR) targeted agents" or "AR-targeted agents" as used herein refers to agents having affinity for the androgen receptor, and particularly functioning as an antagonist by being capable of inhibiting binding of androgenic hormones like testosterone and dihydrotestosterone to the androgen receptor. These agents find a particular use in antihormone therapies, such as for example antitestosterone therapy. Abiraterone acetate or enzalutamide are non-limiting examples of AR-targeted agents.

The term "androgen receptor splice variant V7", and its abbreviation AR-V7, as used herein, refers to a splice variant of the androgen receptor (AR) that comprises a N-terminal transcription/regulatory domain, encoded by exon 1, and most of the two DNA-binding domains, encoded by exons 2 and 3, but lacks a hinge region, encoded by exon 4, and a C-terminal hormone-binding domain and C-terminal region, encoded by exons 5-8. Instead, exon 3 is spliced to a region from within intron 3, referred to as the "CE3 region". The AR-V7 (also termed AR3) variant is constitutively active, meaning that it also activates gene transcription in the absence of testosterone and dihydrotestosterone. The nucleotide sequence of the AR-V7 mRNA encoding region, as provided by GenBank accession number FJ235916, is depicted in FIG. 7. The sequence of the AR-V7-specific CE3 region, starting at nucleotide 2216, is underlined. An in-frame stop codon at position 2263-2265 is indicated in bold.

The term "AR-V7-status", with reference to a patient condition, refers to the presence or absence in prostate cancer cells, preferably in CTCs, of androgen receptor gene-expression products of the AR-V7 variant in the form of RNA or protein.

The term "positive AR-V7 status" as used herein, refers to the presence (vs. absence in the case of a negative status) of androgen receptor mRNA splice variant 7 transcripts in a sample. When using PCR for detection, the presence of AR-V7 transcripts is detected as a difference in the Cq value (i.e. the quantitation cycle or the cycle in which a detectable (fluorescence) signal is obtained) between AR-V7 and a reference transcript or gene, such as the Cq value obtained for the epithelial markers EPCAM and/or KRT19, or the reference genes GUSB, HMBS and HPRT1, preferably EPCAM and/or KRT19. As an example, in a sample having negative AR-V7 status, more cycles are required to detect the AR-V7 target than to detect the epithelial marker EPCAM.

The term "PCR reaction", as is used herein, refers to an amplification reaction that is characterized by repeated cycles of denaturation of target nucleic acid template, annealing of primers, and extension (synthesis) of new nucleic acid strand. The specificity of a PCR reaction is substantially determined by the % identity of the primers to the target nucleic acid template and the annealing temperature. The term "real-time PCR reaction", as is used herein, refers to a PCR amplification reaction to which a labeled probe or a dye is added to generate a signal. The intensity of the signal is a measure for the amount of product that is generated. Detection of the signal in real-time allows quantification of the amount of starting material. A real-time PCR reaction is performed in specialized thermal cyclers with detection systems that detect the signal, for example a LightCycler 480II (Roche Diagnostics, Almere, The Netherlands), a Mastercycler Realplex Ep Real-Time PCR System (Eppendorf A.G., Hamburg, Germany), or a StepOne™ Plus (Thermo Fisher Scientific Inc., Waltham, Mass. USA). However, a separate probe does not need to be present. Some real-time PCR reactions incorporate a dye in the primer (e.g. Scorpion® primers; Premier Biosoft, Palo Alto, Calif., USA) and are comprised in the scope of the present invention.

The terms "forward primer" and "reverse primer", as are used herein, refer to a single-stranded oligonucleotide or oligonucleotide mimic of 15-50 bases, preferably 16-30 bases, that is complementary to nucleic acid sequences flanking the region to be amplified. The sequence of the forward primer and reverse primer determines the specificity of the amplification reaction. Preferred primers are preferably about 100% identical to a region on a target nucleic acid template such that only the region between two primers in a target nucleic acid template is amplified. The distance between the primer binding sites on the target nucleic acid template will determine the size of the amplified product.

The term "probe", as is used herein, refers to a single-stranded oligonucleotide or oligonucleotide mimic of 15-50 bases, preferably 16-30 bases, that is complementary to a nucleic acid sequence within a target nucleic acid, such as a PCR amplicon. A preferred probe is about 100% identical to the target region of a target nucleic acid. A probe generally comprises a detectable label at its 3'- or 5'-end.

The terms "target DNA molecule", "target nucleic acid (template)" and "template DNA molecule", as are used herein, refer to nucleic acid of which a region between two primers, preferably a forward primer and a reverse primer, is amplified. A target nucleic acid template is a gene or a gene product, such as a RNA product, or a part of the gene or part of the gene product.

The term "amplicon", as is used herein, refers to a region on a target nucleic acid template that is amplified using said two primers, preferably a forward primer and a reverse primer. An amplicon preferably comprises a nucleic acid sequence that is complementary to a nucleic acid sequence of a probe that specifically recognizes said amplicon.

The term "specifically hybridize", as is used herein, refers to nucleic acid molecules that form a double stranded nucleic acid molecule under stringent conditions.

The terms "stringency" and "stringent hybridization" refer to hybridization conditions that affect the stability of hybrids, e.g., temperature, salt concentration, pH, and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions may be sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Hybridization procedures are well known in the art and are described by e.g. Ausubel et al., 1998. Current Protocols in Molecular Biology, John Wiley, New York; and Sambrook et al., 2001. Molecular cloning: a laboratory manual. Cold Spring Harbor Laboratory Press, New York.

The term "cabazitaxel", as used herein, refers to a compound belonging to the taxoid family and having the formula:

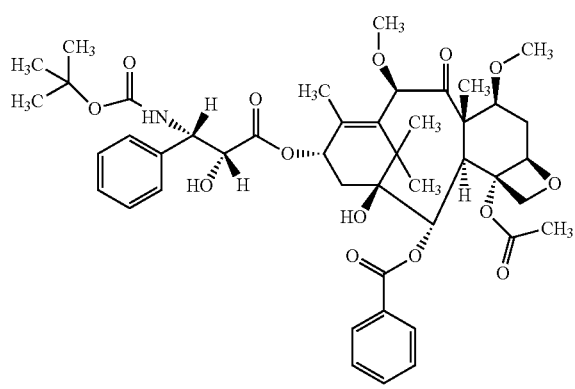 [SMILES: CO[C@H]1C(=O)[C@]2(C)[C@@H](OC)C[C@H]3OC[C@@]3(OC(C)=O)[C@H]2[C@H](OC(=O)c2ccccc2)[C@]2(O)C[C@H](OC(=O)[C@H](O)[C@@H](NC(=O)OC(C)(C)C)c3ccccc3)C(C)=C1C2(C)C]

The chemical name of cabazitaxel is 4a-acetoxy-2a-benzoyloxy-5,20-epoxy-1-hydroxy-7,10-dimethoxy-9-oxo-1 1-taxen-13a-yl (2R,3S)-3-ferf-butoxycarbonylamino-2-hydroxy-3-phenylpropionate. Cabazitaxel is synonymously known as (2a,5,7,10,13a)-4-acetoxy-13-({(2R,3S)-3-[(tert-butoxycarbonyl)amino]-2-hydroxy-3-phenylpropanoyl}oxy)-1-hydroxy-7,10-dimethoxy-9-oxo-5,20-epoxytax-1 1-en-2-yl benzoate.

The compound cabazitaxel and a method for its preparation is described in WO 96/30355, EP 0 817 779 B1 and U.S. Pat. No. 5,847,170, which are incorporated herein by reference in their entirety. Cabazitaxel may be administered in base form (cf. above formula), or in the form of a hydrate. It may also be a solvate, i.e. a molecular complex characterized by the incorporation of the crystallization solvent into the crystal of the molecule of the active principle (see in this respect page 1276 of J. Pharm. Sci. 1975, 64(8), 1269-1288). In particular, it may be an acetone solvate, and, more particularly, may be the solvate described in WO 2005/028462. It may be an acetone solvate of cabazitaxel containing between 5% and 8% and preferably between 5% and 7% by weight of acetone (% means content of acetone/content of acetone+cabazitaxel×100). An average value of the acetone content is 7%, which approximately represents the acetone stoichiometry, which is 6.5% for a solvate containing one molecule of acetone. The following procedure allows for the preparation of an acetone solvate of cabazitaxel: 940 ml of purified water are added at 20±5° C. (room temperature) to a solution of 207 g of 4a-acetoxy-2a-benzoyloxy-5,20-epoxy-1-hydroxy-7,10-dimethoxy-9-oxo-1 1-taxen-13a-yl(2R,3S)-3-ferf-butoxycarbonylamino-2-hydroxy-3-phenylpropionate at about 92% by weight in about 2 litres of acetone, followed by seeding with a suspension of 2 g of 4a-acetoxy-2a-benzoyloxy-5,20-epoxy-1-hydroxy-7,10-dimethoxy-9-oxo-1 1-taxen-13a-yl (2R, 3S)-3-ferf-butoxycarbonylamino-2-hydroxy-3-phenylpropionate isolated from acetone/water in a mixture of 20 ml of water and 20 ml of acetone. The resulting mixture is stirred for about 10 to 22 hours, and 1.5 litres of purified water are added over 4 to 5 hours. This mixture is stirred for 60 to 90 minutes, and the suspension is then filtered under reduced pressure. The cake is washed on the filter with a solution prepared from 450 ml of acetone and 550 ml of purified water, and then oven-dried at 55° C. under reduced pressure (0.7 kPa) for 4 hours. 197 g of 4a-acetoxy-2obenzoyloxy-5,20-epoxy-1-hydroxy-7,10-dimethoxy-9-oxo-1 1-taxen-13oyl (2R,3S)-3-fert-butoxycarbonylamino-2-hydroxy-3-phenylpropionate acetone containing 0.1% water and 7.2% acetone (theoretical amount: 6.5% for a stoichiometric solvate) are obtained.

Cabazitaxel may be administered parenterally, such as via intravenous administration. A galenical form of cabazitaxel suitable for administration by intravenous infusion is that in which the cabazitaxel is dissolved in water in the presence of excipients chosen from surfactants, cosolvents, glucose or sodium chloride, etc. For example, a galenical form of cabazitaxel may be prepared by diluting a premix solution of cabazitaxel contained in a sterile vial (80 mg of cabazitaxel+2 ml of solvent+Polysorbate 80) with a sterile vial containing a solution of 6 ml of water and ethanol (13% by weight of 95% ethanol) in order to obtain 8 ml of a solution ready to be rediluted in a perfusion bag. The concentration of cabazitaxel in this ready-to-redilute solution is about 10 mg/ml. The perfusion is then prepared by injecting the appropriate amount of this ready-to-redilute solution into the perfusion bag containing water and glucose (about 5%) or sodium chloride (about 0.9%).

Cabazitaxel may be administered in combination with a corticoid, such as prednisone or prednisolone, as two distinct pharmaceutical preparations. It may also be administered without prednisone.

Accordingly, one aspect of the invention is a method of treating prostate cancer comprising administering to a patient in need thereof an effective amount of cabazitaxel in combination with a corticoid, such as prednisone or prednisolone.

The combination is administered repeatedly according to a protocol that depends on the patient to be treated (age, weight, treatment history, etc.), which can be determined by a skilled physician. In one aspect of the invention, cabazitaxel is administered by perfusion to the patient according to an intermittent program with an interval between each administration of 3 weeks, which may be prolonged by 1 to 2 weeks depending on the tolerance to the preceding administration. The median number of cycles is 6. The prednisone or prednisolone may be administered daily, for example in the form of one dosage intake per day, throughout the duration of the treatment. Examples of doses for the two antitumoral agents are given in the "Example" section. The currently recommended dose is 25 mg/m$^2$ of cabazitaxel administered as a one-hour infusion and 10 mg per day of prednisone or prednisolone administered orally.

In some aspects of the invention, the patient to be treated expressing a androgen receptor V7 variant has prostate cancer that is resistant to hormone therapy (i.e., hormone refractory) and has previously been treated with docetaxel. In some aspects, the patient has prostate cancer that progressed during or after treatment with docetaxel. In some aspects, the patient was previously treated with at least 225 mg/m$^2$ cumulative dose of docetaxel. In a particular aspect, the patient showed progression of their disease in the six months following hormone therapy or during docetaxel treatment or after docetaxel treatment. In another particular aspect, the patient showed progression of their disease in the three months following hormone therapy or after docetaxel treatment.

In some aspects of the invention, the patient to be treated expressing a androgen receptor V7 variant has a measurable tumour and may show progression of the disease via a metastatic lesion of the viscera or of a soft tissue of at least 1 cm determined by MRI or by an axial tomographic scan (CT scan).

In some aspects of the invention, the patient to be treated expressing a androgen receptor V7 variant has an unmeasurable tumour and may show an increase in the PSA level with three measurements at a 1-week interval or the appearance of new lesions.

In some aspects of the invention, the patient to be treated expressing a androgen receptor V7 variant has undergone castration by orchidectomy or with LHRH agonists, elimination of the androgens or monotherapy with estramustine.

In a preferred aspect, the life expectancy of the patient to be treated should be at least 2 months.

In some aspects, the treatment does not include patients who have previously received mitoxantrone, or who have received less than 225 mg/m$^2$ of docetaxel, or who have undergone a radiotherapy that has eliminated more than 40% of the marrow, who have received a treatment within the 4 weeks preceding the test, who have a neuropathy or a stomatitis, involving the brain or the meninges, who have shown severe hypersensitivity to polysorbate or to prednisone, whose blood analysis shows an appreciable decrease in neutrophils, haemoglobin or platelets, an increase in bilirubin and/or liver enzymes and creatinine, or who have heart problems or an infection requiring antibiotics.

An aspect of the invention comprises increasing the survival of a patient with hormone refractory metastatic prostate cancer, comprising administering to a patient in need thereof a clinically proven effective amount of cabazitaxel, optionally in combination with prednisone or prednisolone. In some preferred aspects of this invention, the patient expressing a androgen receptor V7 variant has previously been treated with a docetaxel-containing regimen. In alternative preferred aspects, the patient expressing a androgen receptor V7 variant has not been previously treated with a docetaxel-containing regimen.

The androgen receptor V7 variant (AR-V7) is a constitutively active variant, meaning that it also activates gene transcription in the absence of testosterone and dihydrotestosterone. AR-V7 comprises the N-terminal transcription/regulatory domain and most of the DNA-binding domains, but lacks a hinge region and a C-terminal hormone-binding domain and C-terminal region. It was recently reported by Antonarakis et al., (Antonarakis et al., 2014. N Engl J Med 371: 1028-1038), that detection of androgen receptor mRNA splice variant 7 (AR-V7) in CTCs from men with mCRPC is associated with resistance to enzalutamide and abiraterone acetate. Hence, AR-V7 status may be used as a biomarker to predict resistance to AR-targeting agents, facilitating treatment selection. Is was further suggested that AR-V7 would also lack a microtubule binding domain, rendering this AR-V7 positive cells also resistant to taxane-mediated treatments such as docetaxel chemotherapy (Portella et al., 2013. Cancer Res 73: 4081; Thadani-Mulero et al., 2014. Cancer Res 74: 2270-82).

It is now shown that, although AR-V7 lacks a microtubule binding domain and AR-V7 positive cells are resistant to taxane-mediated treatments such as docetaxel, AR-V7 positive cells are sensitive to the taxane cabazitaxel. Hence, cabazitaxel still can be used as an effective treatment for AR-V7-positive prostate cancer patients, even in the case that the patients have become resistant to docetaxel.

Further variants of the androgen receptor have been described that comprise the N-terminal transcription/regulatory domain and most of the DNA-binding domains, but lack a hinge region and a C-terminal hormone-binding domain and C-terminal region, similar to AR-V7. These variants include AR-V1, AR-V2, AR-V3, AR-V4, AR-V5, AR-V6, AR-V9, AR-V10, and AR-V11, of which AR-V3, AR-V4 are indicated as being constitutive active, similar to AR-V7 (Lu and Luo, 2013. Trans Androl Urol 2: 178-186).

Side-effects of cabazitaxel therapy and prophylactic measures to avoid and/or manage these side-effects are well known to one of skill in the art and are for instance indicated in detail in WO2011/051894, which publication is incorporated by reference herein in its entirety.

Androgen Receptor Status

The status of the androgen receptor variant V7 in a patient, is preferably determined in a sample comprising cancer cells of the prostate cancer patient. Said sample preferably is a tissue sample such as, for example, a biopsy sample, or a sample of a bodily fluid, preferably urine, lymph or blood, including serum. Said status is most preferably determined in circulating tumor cells (CTCs) that are present in blood or that have been isolated from blood.

CTCs may be captured or isolated from blood using marker-free isolation of CTCs, based on, for example, physical properties such as a larger size and differences in density, charge, and migratory properties, when compared to blood cells such a leukocytes (Karabacak, 2014. Nature Protocols 9, 694-710). CTCs are preferably isolated from a blood sample using specific cell surface markers that are absent from normal blood cells. A preferred marker for epithelial tumor cells is Epithelial Cell Adhesion Molecule (EpCAM), because it is expressed by cells of epithelial origin, but is absent in blood cells or hematocytes. Conjugation of antibodies against EpCAM to magnetic beads, followed by purification of captured cells through a magnetic field, has been used to enrich CTCs from the blood of patients with cancers of the breast, prostate, and colon. Methods and means for the isolation of CTCs from blood are known in the art, including the CytoQuest™ cell retrieval system (Abnova, Taipei City, Taiwan), the Adna Test Prostate Cancer Select kit (AdnaGen, Langenhagen, Germany) and the CellSearch® system (Janssen Diagnostics; South Raritan, N.J. (USA)). Of these, the CellSearch® system, a clinically validated, FDA-cleared system for identification, isolation, and enumeration of circulating tumor cells (CTCs) from blood, is preferred in aspects of this invention due to its sensitivity (detection limit of the AR-V7 assay as described herein was ≥3 epithelial CTCs in the final preparation available for RT-qPCR). The CellSearch® system allows enumeration of CTCs by virtue of the CELL-SEARCH® Circulating Tumor Cell Test, which comprises magnetic separation of CTCs from the bulk of other cells in the blood by using ferrofluid nanoparticles with antibodies that target epithelial cell adhesion; staining of CTCs with epithelial cell-specific cytokeratin monoclonal antibodies; identification of leukocytes that may have contaminated the sample by use of an anti-CD45 monoclonal antibody stain; DAPI DNA staining for labeling the nuclei of both CTCs and leukocytes; concentration of cells in a magnet cartridge that applies a magnetic force that pulls the cells to a single focal depth; and scanning the stained CTCs in the cartridge on an analyzer that displays tumor cell candidates that are positive for cytokeratin and DAPI, optinally followed by final review of an operator of the candidate cells.

Captured cells are preferably visualized by staining with a cocktail of antibodies against the cytoplasmic epithelial cytokeratins (8, 18, and/or 19) and the leukocyte-specific marker CD45. Cells that are positive for CD45 are excluded from enumeration. Prostatic CTCs are defined as the subset of EpCAM-captured cells that are ≥4 µm, with round-to-oval morphology, and positive for cytokeratins and negative for CD45.

A blood sample is preferably processed within 96 hours after the provision of the sample. Said sample is preferably collected into a receptacle containing a preservative that maintains the morphology and cell surface antigen expression of cells. A preferred receptacle is the CellSave® Tube (Janssen Diagnostics; South Raritan, N.J. (USA)).

Said V7 variant status is determined by analysis of RNA expression products and/or protein expression products from prostate cancer cells, preferably from CTCs. To obtain RNA expression products and/or protein expression products, the prostate cancer cells are preferably lysed under conditions that preserve the quality of the RNA and/or protein. Examples of these preservative conditions are RNase inhibitors such as RNAsin® (Pharmingen) or RNasecure® (Ambion), aquous solutions such as RNAlater® (Assuragen), Hepes-Glutamic acid buffer mediated Organic solvent Protection Effect (HOPE), and RCL2 (Alphelys), and non-aquous solutions such as Universal Molecular Fixative (Sakura Finetek USA Inc.).

Methods and means for extraction of proteins from a variety of samples are known in the art, including but not limited to lysis of cells with a mild detergent such as deoxycholic acid, and or a chaotropic agens such as guanidinium chloride, and sodium dodecyl sulfate. Additional reagents that may be included in a protein isolation buffer are a chelator such as EGTA and/or EDTA, a protease inhibitor and a phosphatase inhibitor. Known kits for isolation of proteins from a biological sample include PARIS™ (Life Technologies, Carlsbad, USA), ReadyPrep protein extraction kit (BioRad, Hercules, USA) and Detergent-Free Total Protein Isolation Kit™ (Norgen Biotek, Ontario, Canada). The presence or absence of AR-V7 on the protein level may be determined by polyacrylamide gel electrophoresis, including two dimensional gel electrophoresis, multidimensional protein identification technology, ELISA, liquid chromatography-mass spectrometry (LC-MS), matrix-assisted laser desorption/ionization time-of-flight mass spectrometry (MALDI-TOF). Antibodies that are specific for the AR-V7 variant are commercially available from Precision Antibody, Columbia (USA), and Abcam, Cambridge (UK).

Said V7 variant status is in a particularly preferred embodiment determined by amplification of RNA expression products of the androgen receptor gene in the form of transcripts. For this, RNA may be isolated from prostate cancer cells, preferably CTCs, by any technique known in the art, including but not limited to Trizol (Invitrogen; Carlsbad, Calif.), RNAqueous® (Applied Biosystems/Ambion, Austin, Tx), Qiazol® (Qiagen, Hilden, Germany), AllPrep DNA/RNA Micro Kit (Qiagen, Hilden, Germany), Agilent Total RNA Isolation Lits (Agilent; Santa Clara, Calif.). A preferred RNA isolation procedure involves the use of AllPrep DNA/RNA Micro Kit (Qiagen, Hilden, Germany).

The presence or absence of AR-V7 in tumor cells may be determined by any method known in the art, including Northern blotting, reverse transcription quantitative polymerase chain reaction (RT-qPCR), microarray analysis and RNA sequencing, preferably next generation sequencing. For microarray analysis, a hybridization mixture is prepared by extracting and labelling of RNA. The extracted RNA is preferably converted into a labelled sample comprising either complementary DNA (cDNA) or cRNA using a reverse-transcriptase enzyme and labelled nucleotides. A preferred labelling introduces fluorescently-labelled nucleotides such as, but not limited to, cyanine-3-CTP or cyanine-5-CTP. Examples of labelling methods are known in the art and include Low RNA Input Fluorescent Labelling Kit (Agilent Technologies), MessageAmp Kit (Ambion) and Microarray Labelling Kit (Stratagene). One or more probes that specifically hybridize to a part of the mRNA that encodes the N-terminal transcription/regulatory domain and/ or the DNA-binding domain of the AR-V7 variant can be used to detect RNA expression products of the androgen receptor, while probes that specifically hybridize to a part of the mRNA that encodes the AR-V7-specific region at the C-terminus can be used to detect RNA expression products of the AR-V7 variant.

The presence or absence of AR-V7 is preferably determined by qPCR. For this, messenger RNA (mRNA) is converted into complementary DNA (cDNA) using a reverse transcriptase. The converted cDNA is subsequently amplified by PCR using a pair of primers that specifically hybridize to the target DNA that is to be amplified. The amount of product that is amplified can be quantified using, for example, TaqMan® (Applied Biosystems, Foster City, Calif., USA), Molecular Beacons, Scorpions® and SYBR® Green (Molecular Probes). Quantitative nucleic acid sequence based amplification (qNASBA) can be used as an alternative for qPCR.

The pair of primers that specifically hybridize to the target DNA preferably include a primer that specifically hybridizes to a region of the mRNA that encodes the N-terminal transcription/regulatory domain and/or the DNA-binding domain of AR-V7, preferably to the DNA-binding domain of AR-V7, more preferred a region within exon 3, and a primer that specifically hybridizes to the CE3 region as indicated in FIG. 7. Preferred primers and probes are provided in Table 1.

The present invention provides a method for treating an AR-V7-positive patient suffering from prostate cancer comprising determining the AR-V7-status in said patient and administering cabazitaxel in base form or in the form of an hydrate or a solvate, to a AR-V7-positive patient, in combination with a corticoid. Preferably said prostate cancer is metastatic castration-resistant prostate cancer (mCRPC).

In another preferred embodiment of a method for treating an AR-V7-positive patient suffering from prostate cancer as described above, the step of determining the AR-V7-status in said patient is performed on isolated tumor cells, preferably on CTCs.

In yet another preferred embodiment of a method for treating an AR-V7-positive patient suffering from prostate cancer, the step of determining the AR-V7-status in said patient is performed on isolated CTCs using the CELL-SEARCH® Circulating Tumor Cell Test. In such a method for treating patients the patient has preferably been previously treated with a docetaxel-based regimen, and said patient is preferably resistant to docetaxel, and/or abiraterone acetate and/or enzalutamide.

In another preferred embodiment, of a method as described above, the patient has not been pretreated with docetaxel and/or AR-targeted agents, or wherein said patient, when pretreated with docetaxel and/or AR-targeted agents has not yet become resistant to docetaxel and/or AR-targeted agents.

The present invention also provides the use of cabazitaxel in base form or in the form of an hydrate or a solvate in combination with a corticoid for the manufacture of a medicament for treating a patient suffering from prostate cancer, wherein said patient is an AR-V7-positive patient and wherein said use further comprises determining the AR-V7-status in said patient, preferably said prostate cancer is metastatic castration-resistant prostate cancer (mCRPC).

In another preferred use of cabazitaxel for the manufacture of a medicament according to the present invention, the AR-V7-status in said patient is determined on isolated tumor cells, preferably CTCs. In still another preferred use of cabazitaxel for the manufacture of a medicament according to the present invention, said step of determining the AR-V7-status in said patient is performed on isolated CTCs using the CELLSEARCH® Circulating Tumor Cell Test.

In still another preferred use of cabazitaxel for the manufacture of a medicament according to the present invention said patient has been previously treated with a docetaxel-based regimen.

In yet another preferred use of cabazitaxel for the manufacture of a medicament according to the present invention, said patient is resistant to docetaxel.

In still another preferred use of cabazitaxel for the manufacture of a medicament according to the present invention said patient is resistant to abiraterone acetate and/or enzalutamide.

In still a further preferred use of cabazitaxel for the manufacture of a medicament according to the present invention said patient has not been pretreated with docetaxel and/or AR-targeted agents, or wherein said patient, when pretreated with docetaxel and/or AR-targeted agents has not yet become resistant to docetaxel and/or AR-targeted agents.

The invention further provides a method of identifying patients with prostate cancer, in particular patients with mCRPC, who are eligible for treatment with cabazitaxel in base form or in the form of an hydrate or a solvate, in combination with a corticoid, the method comprising testing a biological sample from the patient for the presence of AR-V7 tumor cells, wherein the patient is eligible for treatment with said cabazitaxel if said tumor cells in said sample test positive for AR-V7. Said method may assist in the identification and/or classification of patients that are likely to benefit from treatment with cabazitaxel in base form or in the form of an hydrate or a solvate, in combination with a corticoid.

Said tumor cell preferably are circulating tumor cells, that are circulating in a bodily fluid of the patient, preferably urine and/or blood, including serum. The circulating tumor cells are preferably separated from essentially all other cells in said sample using a marker that is expressed by the tumor cells, but that is not expressed, or not expressed at detectable levels, by all other cells in said sample.

Hence, a preferred method of the invention involves the provision of a blood, serum and/or urine sample from the patient, and separating tumor cells from other cells that are present in said sample using a marker that is expressed by the tumor cells, but that is not expressed, or not expressed at detectable levels, by all other cells in said sample.

Said marker preferably is a marker that is expressed on the surface of tumor cells, preferably on all or most tumor cells. A preferred marker for epithelial tumor cells, such as prostate cells, is EpCAM. Said marker preferably is specifically recognized by an antibody. The term "specifically recognized" means that the Kd of an antibody for binding to the marker is less than about 10 fold, 50 fold or 100 fold the Kd for its binding to, e.g., an unrelated marker, as determined using an assay known to one of skill in the art such as a BIAcore assay.

The determination that a particular antibody binds specifically to the marker may alternatively readily be made by using or adapting routine procedures. One suitable assay makes use of the Western blotting procedure (described in many standard texts, including "Antibodies, A Laboratory Manual" by Harlow and Lane). To determine that a given marker-binding antibody binds specifically to the marker, total cellular protein is extracted from cells that do not express the marker, such as, for example, a non-epithelial cell such as a lymphoid cell, transformed with a nucleic acid molecule encoding the marker. As a negative control, total cellular protein is also extracted from corresponding non-transformed cells. These protein preparations are then electrophorezed on a non-denaturing or denaturing polyacrylamide gel. Thereafter, the proteins are transferred to a membrane (for example, a nitrocellulose membrane) by Western blotting, and the agent to be tested is incubated with the membrane. After washing the membrane to remove non-specifically bound agent, the presence of bound agent is detected by the use of an antibody raised against the test agent conjugated to a detection agent, such as the enzyme alkaline phosphatase; application of the substrate 5-bromo-5 4-chloro-3-indolyl phosphate/nitro blue tetrazolium results in the production of a dense blue compound by immunolocalized alkaline phosphatase. Agents which bind specifically to the marker will, by this technique, be shown to bind to the marker band (which will be localized at a given position on the gel determined by its molecular mass) in the extract from the transformed cells, whereas little or no binding will be observed in the extract from non-transformed cells. Non-specific binding of the antibody to other proteins may occur and may be detectable as a weak signal on the Western blots. The nonspecific nature of this binding will be recognized by one skilled in the art by the weak signal obtained on the Western blot relative to the strong primary signal arising from the specific antibody-marker binding. Ideally, a marker binding antibody would not bind to proteins extracted from the non-transformed cells. In addition to binding assays using extracted proteins, putative marker-binding antibodies may be tested to confirm their ability to bind substantially only said marker in vivo by conjugating the antibody to a fluorescent tag (such as FITC) and analyzing its binding to epithelial cells and non-epithelial cells such as such as, for example, lymphoid cells, by Fluorescence Activated Cell Sorting (FACS). An antibody which binds substantially only the marker will stain only the epithelial cells.

It will be understood that the term "antibody", as used herein, refers to a polyclonal or monoclonal whole immunoglobulin, e.g., IgG, IgM, IgA, IgE and the like, or an immunoglobulin fragment, e.g., isolated CDR regions; single chain Fv molecules ("scFv"), wherein a VH domain and a VL domain are linked by a peptide linker that allows the two domains to associate to form a binding domain, diabody (Hollinger et al., 1993. PNAS USA 90: 6444-6448), F(ab)2, F(ab')2, Fab, Fab' and the like, or a mixture thereof. Antibodies and antibody fragments which specifically bind a wide variety of ligands are known, and many of these are disclosed in the patents whose disclosures are incorporated herein by reference. Many antibodies and antibody fragments which specifically bind tumor-associated markers are disclosed in, e.g., U.S. Pat. Nos. 4,348,376, 4,361,544, 4,331,647, 4,468,457, 4,444,744, 4,460,559 and 4,460,561, the disclosures of which are incorporated herein by reference. In addition, the term "antibody" includes artificial antibody-like molecules or antibody mimetics such as AFFIBODY® molecules (Nord et al., 1995. Prot Eng 8: 601-608), ANTICALINS® (Skerra, 2008. FEBS J. 275: 2677-2683), and AVIMERS® (Silverman et al., 2005. Nat Biotechnol 23: 1556-1561).

Said antibody preferably is used to capture cells that are bound to the antibody, thereby separating tumor cells from other cells in said sample by any method known in the art. For example, an antibody that reacts with the marker antibody may be bound to a surface, allowing to capture the marker-antibody complex and associated cells onto the surface. As an alternative, Protein A or Protein G can be used, especially if the marker antibody is an IgG antibody.

Said marker antibody preferably is labeled with a detectable label. Said detectable label is a label that is detectable by spectroscopic, photochemical, biochemical, immunochemical, or chemical means. For example, useful labels include radioactive labels, fluorescent labels, electron-dense reagents, enzymes (as commonly used in ELISAs), biotin, or haptens and proteins for which antisera or monoclonal antibodies are available.

Said label preferably is a label that allows magnetically separating said tumor cells. For this, the antibody is preferably labeled with ferrofluid nanoparticles. Preferred ferrofluid nanoparticles are made of nanometric-sized iron oxide particles, which may be encapsulated or glued together with polymers. Suitable magnetic particles include DYNABEADS® (Life Technologies, Carlsbad, Calif., USA), MICROBEADS®, for example in combination with MACS® Column Technology (Miltenyi Biotec Inc., Auburn, Calif., USA) and streptavidin-coupled NanoLink™ and MagnaLink™ Beads (Solulink Inc., San Diego, Calif., USA).

The captured tumor cell faction will be enriched for tumor cells, relative to other cells that are present in the biological sample of the patient. Said captured tumor cells may optionally be enumerated by staining the tumor cells in a sample comprising the captured, enriched tumor cells with a nuclear DNA stain, preferably DAPI, and a cytokeratin-specific antibody, preferably a monoclonal antibody, specific to epithelial cells, preferably anti-cytokeratin 8/18/19, while optionally differentiating said dual stained tumor cells from stained leukocytes in said sample using a leukocyte-specific anti-CD45 monoclonal antibody stain. Methods and means for staining cells using a nuclear DNA stain and/or antibodies are known in the art and are available, for example, from Life Technologies (Life Technologies, Carlsbad, Calif.), Abcam (Cambridge, Mass., USA) and Dako (Agilent Technologies, Glostrup, Denmark).

The presence of androgen receptor mRNA splice variant 7 transcripts in said enriched tumor cells may be determined by methods known in the art, including the use of commercially available antibodies that are specific for the AR-V7 variant, such as from Precision Antibody, Columbia (USA), and Abcam, Cambridge (UK).

Said V7 variant status is preferably determined by amplification of RNA expression products of the androgen receptor gene. For this, RNA may be isolated from prostate cancer cells, preferably CTCs, by any technique known in the art, including but not limited to Trizol (Invitrogen; Carlsbad, Calif.), RNAqueous® (Applied Biosystems/Ambion, Austin, Tx), Qiazol® (Qiagen, Hilden, Germany), AllPrep DNA/RNA Micro Kit (Qiagen, Hilden, Germany), Agilent Total RNA Isolation Lits (Agilent; Santa Clara, Calif.). A preferred RNA isolation procedure involves the use of AllPrep DNA/RNA Micro Kit (Qiagen, Hilden, Germany).

Following isolation, RNA expression products are reverse transcribed into complementary DNA (cDNA) by a RNA dependent DNA polymerase such as M-MLV reverse transcriptase, or a modified reverse transcriptase such as Superscript® reverse transcriptase (Invitrogen; Carlsbad, Calif.), Superscript® VILO™ cDNA synthesis (Invitrogen; Carlsbad, Calif.), and the Quantiscript Reverse Transcriptase (Qiagen, Hilden, Germany). Said cDNA may be synthesized using random primers, for example hexamers or nonamers, or gene-specific primers such as primers that are complementary to the AR-V7-specific CE3 region, which is underlined in FIG. 7. The generation of complementary DNA (cDNA), pre-amplification, and RT-qPCR are preferably performed as described before (Sieuwerts et al., 2009. Breast Cancer Res Treat 118:455-68; Sieuwerts et al., 2011. Clin Cancer Res 17:3600-18; which are incorporated herein by reference).

The invention further provides a kit of parts for determining the AR-V7-status in isolated tumor cells, preferably isolated circulating tumor cells, in a bodily fluid of a patient suffering from prostate cancer. Said bodily fluid preferably is one of a blood, serum or urine sample obtained from said patient. Said kit preferably comprises amplification primers for reverse transcription and amplification of a complementary DNA product of androgen receptor mRNA splice variant 7 transcripts by reverse transcription coupled to quantitative polymerase chain reaction (RT-qPCR). Said kit preferably comprises antibodies that target epithelial cell markers, preferably anti-EpCAM antibodies loaded with ferrofluid nanoparticles, for enriching tumor cells from essentially all other cells in the patient sample by magnetic separation. Said kit optionally further comprises instructions for determining the eligibility of the patient with prostate cancer to treatment with cabazitaxel based on the diagnostic test result results for the AR-V7-status obtained, and/or instructions for treating said patient with cabazitaxel.

For the purpose of clarity and a concise description, features are described herein as part of the same or separate aspects and preferred embodiments thereof, however, it will be appreciated that the scope of the invention may include embodiments having combinations of all or some of the features described.

The invention will now be illustrated by the following example, which is provided by way of illustration and not of limitation and it will be understood that many variations in the methods described and the amounts indicated can be made without departing from the spirit of the invention and the scope of the appended claims.

TABLE 1

Details of the assays used in the RT-qPCRs.

| qPCR name | Gene Symbol | Approved Gene Name | Order Location | info Applied Biosystems | F sequence | R sequence | (FAM_MGB1_NFQ) | Exon boundary | Product size (bp) | Accession code qPCR |
|---|---|---|---|---|---|---|---|---|---|---|
| AR_WT | AR | androgen recpetor | Xq12 | Hs00171 172_m1 | | | AGGCCTTGCCTGGC TTCCGCAACTT | 4 -> 5 | 72 | NM_000044.3 |

TABLE 1-continued

Details of the assays used in the RT-qPCRs.

| qPCR name | Gene Symbol | Approved Gene Name | Location | Order info Applied Biosystems Sequence | F sequence | R sequence | Sequence (FAM_MGB1_NFQ) | Exon boundary | Product size (bp) | Accession code qPCR |
|---|---|---|---|---|---|---|---|---|---|---|
| AR-WT/fl | AR | androgen receptor | Xq12 | AIRSAW0 | CTGCTCAAGAATCATTTCCGTCCGTGCAGCCTAT | CGCTTCTA | GAAAGTCCA TGCGAG | 7 -> 8 | 132 | NM_000044.3 |
| AR-V7 | AR | androgen receptor protein tyrosine | Xq12 | AIPAEKK | GTCCATCTTGGCAAGTCAGCGGGAGAAAAATTCC TCGTCTTC | CTTTCTTCA GGGTTGGC | | 3 -> CE3 | 117 | FJ235916 |
| CD45 | PTPRC | phosphatase, receptor type, C epithelial | 1q31-q32 | Hs00236304_m1 | | | AGAGGCTGAATTCC AGAGACTTCCT | 26 -> 27 | 81 | NM_002838.4 |
| EPCAM | EPCAM | cell adhesion molecule | 2p21 | XXXXXX | AGTTTGCGGAAATACTCGTGAAGGAGATCACAAC CTGCACTTCAATAAATTTTGGCGT | GATCCA | | 4/5 -> 5 | 72 | NM_002354 |
| KRT19 | KRT19 | keratin 19 | 17q21.2 | Hs01051611_gH | | | ACAGCTGAGCATGA AAGCTGCCTTG | 5 -> 6 | 66 | NM_002276.4 |
| GUSB | GUSB | glucuronidase, beta hydroxym | 7q11.21 | Hs99999908_m1 | | | TGAACAGTCACCGA CGAGAGTGCTG | 11 -> 12 | 81 | NM_000181.3 |
| HMBS | HMBS | ethylbilane synthase hypoxanthine | 11q23.3 | Hs00609297_m1 | | | ATGCGGCTGCAACG GCGGAAGAAAA | 1 -> 2 | 64 | NM_001258208.1 |
| HPRT1 | HPRT1 | phosphoribosyltransferase 1 | Xq26.2 | XXXXXX | TTCCTTGGTCGGTCCTTTTCAGATGGTCAAGGTC AGGCAGTATAACCAGCAAGCGC | ATCC | T | 6 -> 7 | 64 | NM_000194 |

TABLE 2

RT-qPCR data of all tested samples. Five healthy blood donors and 11 breast and prostate cancer cell lines - pure and after spiking-in healthy blood donor blood and CellSearch enrichment - served as negative and positive controls (an undetectable (negative) or detectable (positive) PCR signal above the quantitative threshold (Cq) no later than 15 cycles after the average Cq of EPCAM and KRT19). In total 44 patient samples were tested, of which 29 were of sufficient quality to be entered in the analyses. After CellSearch enrichment, an aliquot of 11% was used for the assessment of AR-V7 status. The calculated final number of CTCs used for the PCR analysis was derived from the equation of the regression line of the correlation between the CTC count from 7.5 mL blood - as measured by CellSearch enumeration, from the CellSave tube - and the average Cq of EPCAM and KRT19 (FIG. 4A), thereby taking into account that only 11% of the original sample was used

| Sample description CellSearch enrichment | Theoretical nr of cell line cells/CTCs in PCR | | Mean Cq reference genes* | | Mean Cq epithelial genes** | | Calculated nr of epithelial cells in PCR | | ΔCq AR-WT***± (Cq epithelial-Cq AR-WT) | | ΔCq AR-V7± (Cq epithelial - Cq AR-V7) | |
|---|---|---|---|---|---|---|---|---|---|---|---|---|
| | before | after | before | after | before | after | before | after | before | after | before | after |
| Cell lines | | | | | | | | | | | | |
| PC3 | 20 | 2 | 19.28 | 25.85 | 15.86 | 22.26 | 28 | 3 | no Cq | no Cq | no Cq | no Cq |
| MPE600 | 66 | 7 | 20.41 | 23.86 | 15.61 | 23.35 | 103 | 7 | −7.47 | no Cq | no Cq | no Cq |
| ZR75.1 | 66 | 7 | 17.05 | 24.28 | 12.98 | 22.67 | 254 | 9 | −3.55 | no Cq | −14.68 | no Cq |
| MDA-MB-415 | 66 | 7 | 18.94 | 23.21 | 14.62 | 20.52 | 145 | 19 | −2.83 | −2.55 | no Cq | no Cq |
| CAMA1 | 66 | 7 | 17.03 | 24.35 | 13.86 | 20.97 | 188 | 16 | −2.75 | −2.11 | no Cq | no Cq |
| MDA-MB-453 | 20 | 2 | 21.12 | 25.07 | 17.86 | 23.89 | 14 | 2 | −1.48 | −1.48 | no Cq | no Cq |
| SUM185PE | 66 | 7 | 18.33 | 22.49 | 14.07 | 20.19 | 175 | 21 | −0.66 | −0.68 | −9.90 | no Cq |
| LNCaP* | 66 | 7 | 15.99 | 23.04 | 17.92 | 24.84 | 46 | 4 | 4.14 | 4.30 | −7.79 | no Cq |
| LNCaP* | 20 | 2 | 17.40 | 24.30 | 19.58 | 25.68 | 8 | 1 | 4.06 | 3.14 | −8.09 | no Cq |

TABLE 2-continued

RT-qPCR data of all tested samples. Five healthy blood donors and 11 breast and prostate cancer cell lines -
pure and after spiking-in healthy blood donor blood and CellSearch enrichment - served as negative and positive
controls (an undetectable (negative) or detectable (positive) PCR signal above the quantitative threshold (Cq)
no later than 15 cycles after the average Cq of EPCAM and KRT19). In total 44 patient samples were tested,
of which 29 were of sufficient quality to be entered in the analyses. After CellSearch enrichment, an aliquot
of 11% was used for the assessment of AR-V7 status. The calculated final number of CTCs used for the PCR analysis
was derived from the equation of the regression line of the correlation between the CTC count from 7.5 mL blood -
as measured by CellSearch enumeration, from the CellSave tube - and the average Cq of EPCAM and KRT19 (FIG.
4A), thereby taking into account that only 11% of the original sample was used

| Sample description CellSearch enrichment | Theoretical nr of cell line cells/CTCs in PCR | | Mean Cq reference genes* | | Mean Cq epithelial genes** | | Calculated nr of epithelial cells in PCR | | ΔCq AR-WT***± (Cq epithelial-Cq AR-WT) | | ΔCq AR-V7± (Cq epithelial - Cq AR-V7) | |
|---|---|---|---|---|---|---|---|---|---|---|---|---|
| | before | after | before | after | before | after | before | after | before | after | before | after |
| VCaP | 66 | 7 | 19.21 | 23.93 | 17.82 | 24.17 | 48 | 5 | 4.19 | 4.59 | −4.19 | −5.77 |
| 22RV1 | 20 | 2 | 19.97 | 23.55 | 18.83 | 23.32 | 10 | 2 | −0.11 | 0.12 | −4.97 | −3.57 |
| Healthy blood donors | | | | | | | | | | | | |
| HBD-1 | | 0 | | 23.75 | | 29.26 | | 1 | | no Cq | | no Cq |
| HBD-2 | | 0 | | 25.34 | | no Cq | | 0 | | no Cq | | no Cq |
| HBD-3 | | 0 | | 28.89 | | no Cq | | 0 | | no Cq | | no Cq |
| HBD-4 | | 0 | | 24.89 | | 29.97 | | 1 | | no Cq | | no Cq |
| HBD-5 | | 0 | | 18.62 | | 28.79 | | 1 | | 1.45 | | no Cq |
| Patients | | | | | | | | | | | | |
| CTC1155 | | 68 | | 19.89 | | 16.82 | | 68 | | 0.84 | | −10.30 |
| CTC1172 | | 8 | | 23.60 | | 21.24 | | 15 | | 2.31 | | −8.67 |
| CTC1167 | | 10 | | 18.20 | | 21.41 | | 14 | | 1.79 | | −7.98 |
| CTC1184 | | 38 | | 22.47 | | 21.82 | | 12 | | 0.50 | | −6.93 |
| CTC1170 | | 19 | | 22.45 | | 21.82 | | 12 | | 3.32 | | −8.61 |
| CTC1143 | | 7 | | 21.93 | | 22.20 | | 11 | | 3.31 | | −7.86 |
| CTC1175 | | 21 | | 21.22 | | 22.52 | | 10 | | −0.08 | | no Cq |
| CTC1186 | | 34 | | 23.43 | | 22.54 | | 9 | | 3.34 | | −7.79 |
| CTC1152 | | 2 | | 18.12 | | 22.65 | | 9 | | 0.32 | | −10.00 |
| CTC1183 | | 6 | | 18.99 | | 22.74 | | 9 | | 4.52 | | −8.01 |
| CTC1151 | | 28 | | 25.29 | | 22.74 | | 9 | | −2.42 | | no Cq |
| CTC1147 | | 3 | | 17.72 | | 22.77 | | 9 | | −0.71 | | −7.24 |
| CTC1180 | | 10 | | 19.07 | | 22.80 | | 9 | | −0.12 | | −8.10 |
| CTC1159 | | 4 | | 24.73 | | 23.12 | | 8 | | −0.21 | | no Cq |
| CTC1169 | | 7 | | 19.64 | | 23.12 | | 8 | | 1.17 | | no Cq |
| CTC1134 | | 6 | | 24.83 | | 23.57 | | 7 | | 3.96 | | no Cq |
| CTC1160 | | 25 | | 25.24 | | 24.16 | | 5 | | 2.51 | | no Cq |
| CTC1181 | | 3 | | 24.95 | | 24.51 | | 5 | | 2.21 | | −6.31 |
| CTC1164 | | 7 | | 24.32 | | 24.58 | | 5 | | 3.29 | | −6.41 |
| CTC1148 | | 4 | | 25.19 | | 24.72 | | 4 | | −0.50 | | no Cq |
| CTC1179 | | 10 | | 24.57 | | 24.84 | | 4 | | 0.59 | | no Cq |
| CTC1166 | | 1 | | 20.54 | | 25.08 | | 4 | | 1.14 | | no Cq |
| CTC1156 | | 2 | | 21.56 | | 25.20 | | 4 | | 3.11 | | no Cq |
| CTC1157 | | 2 | | 21.94 | | 25.27 | | 4 | | 3.38 | | −6.20 |
| CTC1176 | | 3 | | 22.57 | | 26.21 | | 3 | | 3.89 | | no Cq |
| CTC1174 | | 1 | | 24.65 | | 26.23 | | 3 | | 0.48 | | no Cq |
| CTC1168 | | 13 | | 26.11 | | 26.28 | | 3 | | 1.56 | | no Cq |
| CTC1161 | | 4 | | 20.41 | | 26.33 | | 3 | | 1.03 | | −4.53 |
| CTC1171 | | 5 | | 23.79 | | 26.36 | | 3 | | 4.62 | | −5.01 |
| Patients not used in the final analysis due to a too low RNA and/or epithelial input (Cq > 26.5) in the final RT-qPCR | | | | | | | | | | | | |
| CTC1145 | | 3 | | 26.28 | | 28.72 | | 1 | | 2.54 | | no Cq |
| CTC1149 | | 1 | | 27.40 | | 29.49 | | 0 | | 1.50 | | no Cq |
| CTC1165 | | 3 | | 27.46 | | 26.69 | | 0 | | 3.35 | | no Cq |
| CTC1185 | | 1 | | 24.64 | | 26.65 | | 2 | | −8.30 | | no Cq |
| CTC1182 | | 8 | | 23.92 | | 26.70 | | 2 | | −0.15 | | no Cq |
| CTC1153 | | 1 | | 22.68 | | 26.87 | | 2 | | −0.89 | | no Cq |
| CTC1162 | | 1 | | 22.16 | | 27.10 | | 2 | | 1.49 | | no Cq |
| CTC1158 | | 8 | | 27.70 | | 27.14 | | 0 | | −0.28 | | no Cq |
| CTC1163 | | 1 | | 19.85 | | 27.61 | | 2 | | 1.46 | | no Cq |
| CTC1154 | | 1 | | 21.29 | | 27.70 | | 2 | | −0.22 | | no Cq |
| CTC1150 | | 1 | | 23.15 | | 28.27 | | 1 | | 2.90 | | no Cq |
| CTC1177 | | 4 | | 22.12 | | 28.48 | | 1 | | 2.17 | | no Cq |
| CTC1178 | | 1 | | 19.02 | | 29.09 | | 1 | | 3.30 | | no Cq |

TABLE 2-continued

RT-qPCR data of all tested samples. Five healthy blood donors and 11 breast and prostate cancer cell lines - pure and after spiking-in healthy blood donor blood and CellSearch enrichment - served as negative and positive controls (an undetectable (negative) or detectable (positive) PCR signal above the quantitative threshold (Cq) no later than 15 cycles after the average Cq of EPCAM and KRT19). In total 44 patient samples were tested, of which 29 were of sufficient quality to be entered in the analyses. After CellSearch enrichment, an aliquot of 11% was used for the assessment of AR-V7 status. The calculated final number of CTCs used for the PCR analysis was derived from the equation of the regression line of the correlation between the CTC count from 7.5 mL blood - as measured by CellSearch enumeration, from the CellSave tube - and the average Cq of EPCAM and KRT19 (FIG. 4A), thereby taking into account that only 11% of the original sample was used

| Sample description CellSearch enrichment | Theoretical nr of cell line cells/CTCs in PCR | | Mean Cq reference genes* | | Mean Cq epithelial genes** | | Calculated nr of epithelial cells in PCR | | ΔCq AR-WT***± (Cq epithelial-Cq AR-WT) | | ΔCq AR-V7± (Cq epithelial - Cq AR-V7) | |
|---|---|---|---|---|---|---|---|---|---|---|---|---|
| | before | after | before | after | before | after | before | after | before | after | before | after |
| CTC1173 | | 1 | | 20.29 | | 29.37 | | 1 | | 3.49 | | no Cq |
| CTC1144 | | 10 | | 21.12 | | no Cq | | 0 | | 4.00 | | no Cq |

*Average Cq values of the reference genes GUSB, HMBS and HPRT1.
**Average Cq value of the epithelial markers EPCAM and KRT19.
***Average Cq value of 2 different assays measuring AR-WT.
±A positive values indicates a PCR signal was detected before the emergence of the epithelial signal, a negative value indicates a PCR signal was detected after the emergence of the epithelial signal.
^Technical replicates of the same RNA sample.

Example

Introduction

In this study, we investigated the predictive value of AR-V7 in CTCs for response to cabazitaxel in docetaxel-pretreated mCRPC patients. We have set up a highly specific RT-qPCR assay to measure mRNA expression levels of wild-type AR (AR-WT) and AR-V7 in CTCs enriched by the CellSearch System (Janssen Diagnostics LLC, Raritan, N.J.). Extensive and robust data are available concerning the clinical relevance of CTCs enumerated by this relatively widely available and Food and Drug Administration (FDA)-approved technique from mCRPC patients. Next, we investigated the predictive and prognostic value of the presence of AR-V7 in CTCs taken before start of cabazitaxel with the aim to establish whether cabazitaxel remains a valid treatment option for AR-V7-positive patients.

Methods

Patients

Patients with mCRPC were recruited from an ongoing prospective multicenter, randomized phase II trial, investigating the effects of oral budesonide on cabazitaxel toxicity (CABARESC, Dutch Trial Registry Number NTR2991). All patients previously received docetaxel and were required to have progression of disease as defined by three rising PSA measurements at least two weeks apart or a PSA rise of ≥2.0 µg/L, or radiological disease progression. Full inclusion and exclusion criteria are listed as follows:

Inclusion Criteria:
  Metastatic castrate resistant prostate cancer with documented disease progression, defined as:
    Rising PSA levels; at least two consecutive rises over a reference value and at least one week apart, or a PSA rise of ≥2.0 µg/L
    Appearance of new lesions or documented disease progression on a CT scan or bone scan
  Previous treatment with docetaxel
  Age ≥18 years
  WHO performance status ≤1
  Adequate renal function (serum creatinine ≤1.5× upper limit of normal (ULN) and/or MDRD calculated creatinine clearance ≥50 mL/min) and hepatic function (total bilirubin ≤1.0×ULN, alanine aminotransferase and aspartate aminotransferase ≤2.5×ULN, or in case of liver metastases ≤5×ULN, and alkaline phosphatase <5×ULN, or in case of bone metastases <10×ULN), within 21 days before randomization
  Adequate hematological blood counts (absolute neutrophil count ≥1.5×10$^9$/L and platelets ≥100×10$^9$/L) within 21 days before randomization
  Castration, either surgically or by continued LHRH agonist therapy
  Written informed consent according to ICH-GCP Exclusion Criteria:
  Impossibility or unwillingness to take oral drugs
  Serious illness or medical unstable conditions requiring treatment, symptomatic central nervous system metastases or history of a psychiatric disorder that would hinder the understanding and obtaining of informed consent
  Use of medications or dietary supplements known to induce or inhibit CYP3A
  Use of hormonal agents other than GnRH agonists
  Known hypersensitivity to corticosteroids
  Any active systemic or local bacterial, viral, or fungal infection
  Ulcerative colitis, Crohn's disease, or celiac disease (active or in medical history)
  Ostomy
  Planned/active simultaneous yellow fever vaccine
  Geographical, psychological, or other non-medical conditions interfering with follow-up All patients in both treatment arms receive the standard dose of cabazitaxel of 25 mg/m$^2$. Cabazitaxel treatment was continued until progression (at the discretion of the treating physician), unacceptable toxicity, or until ten cycles had been administered. The collection of CTC samples was a side-study of the CABARESC trial. For this study, we selected patients included between August 2012 and August 2014 and with ≥10 CTCs/7.5 mL blood before start of cabazitaxel to ensure robust and CTC-specific downstream analysis (FIG. 1). The Erasmus MC and local Institutional Review Boards approved the study (METC 11-324). All patients provided written informed consent for the main study as well as for the side-study on CTC enumeration and characterization.

Sample Processing

Blood was drawn by venipuncture before start of the first and the third cycle of cabazitaxel. Enumeration of CTCs was carried out as described in detail before (Sieuwerts et al., 2009. Breast Cancer Res Treat 118:455-68; Sieuwerts et al., 2011. Clin Cancer Res 17:3600-18). Briefly, CTCs were enumerated from 7.5 mL of blood drawn into a CellSave Preservative tube (Janssen Diagnostics). Blood samples were processed within 96 hours using the Epithelial Cell Kit on the CellSearch System (both Janssen Diagnostics). In this system, epithelial cells are immunomagnetically enriched from whole blood using anti-EpCAM antibodies loaded with ferrofluid nanoparticles. Enriched cells are stained with the nuclear dye 4',6-diamidino-2-phenylindole (DAPI), anti-cytokeratin 8/18/19 labeled with phycoerythrin (PE), and anti-CD45 labeled with allophycocyanin (APC), followed by scanning using the CellTracks Analyzer (Janssen Diagnostics). All cells ≥4 μm, with round-to-oval morphology, positive for cytokeratin and DAPI, with at least 50% overlap in the DAPI and cytokeratin signal, and negative for CD45 were considered CTCs. All samples were analyzed by two independent, trained reviewers.

For molecular characterization of CTCs, 7.5 mL of blood from an EDTA tube was processed using the CellSearch Profile Kit (Janssen Diagnostics) within 24 hours to limit mRNA degradation. No staining step was performed after the immunomagnetical enrichment. Instead, buffer was aspirated after incubation in a hand magnet and enriched cells were lysed in buffer RLT+ (Qiagen, Valencia, Calif.), followed by storage at −80° C. until subsequent RNA isolation using the AllPrep DNA/RNA Micro Kit (Qiagen). After dilutions for cDNA synthesis and pre-amplification, expression levels of AR-WT and AR-V7 were measured by RT-qPCR in an 11% aliquot of the original starting material using Taqman Gene Expression Assays (Applied Biosystems, Carlsbad, Calif.; Table 1). The generation of complementary DNA (cDNA), preamplification, and RT-qPCR were essentially performed as described before (Sieuwerts et al., 2009. Breast Cancer Res Treat 118:455-68; Sieuwerts et al., 2011. Clin Cancer Res 17:3600-18). Details of this test were as follows: For molecular characterization of CTCs, 7.5 mL of blood from an EDTA tube was processed using the CellSearch Profile Kit (Janssen Diagnostics) within 24 hours to limit mRNA degradation. No staining step was performed after the immunomagnetical enrichment. Instead, buffer was aspirated after incubation in a hand magnet and enriched cells were lysed in buffer RLT+ (Qiagen, Valencia, Calif.), followed by storage at −80° C. until subsequent RNA isolation using the AllPrep DNA/RNA Micro Kit (Qiagen).

Of the resulting 12 μL with >200 bp RNA, 5 μL was used for the generation of 10 μL cDNA (RevertAid H Minus First Strand cDNA Synthesis Kit from Thermo Fisher Scientific, Waltham, Mass.), followed by an RNAse H step (Ambion, Life Technologies) to degrade the remaining RNA. Next, 3 μL of the cDNA was used to specifically pre-amplify the transcripts generated by the nine Taqman assays depicted in Table 1, which was done in 14 cycles according the protocol supplied by the manufacturer of the Taqman PreAmp Master Mix kit (Life Technologies, Carlsbad, Calif.). Following pre-amplification, the resulting 12 μL sample was 15-fold diluted prior to 35 cycles of RT-qPCR using a Mx3000P Real-Time PCR System (Agilent, Amsterdam, The Netherlands). For each sample, nine individual PCR reactions were performed in a final volume of 20 μL containing 5 μL diluted, pre-amplified cDNA, 30-50% (V/V) Taqman Universal Mastermix (4326614, Life Technologies), and 0.5-1 μL Taqman gene expression assay, which was done in 35 cycles according the protocol supplied by the manufacturer of the Taqman assays.

Figure 4A:
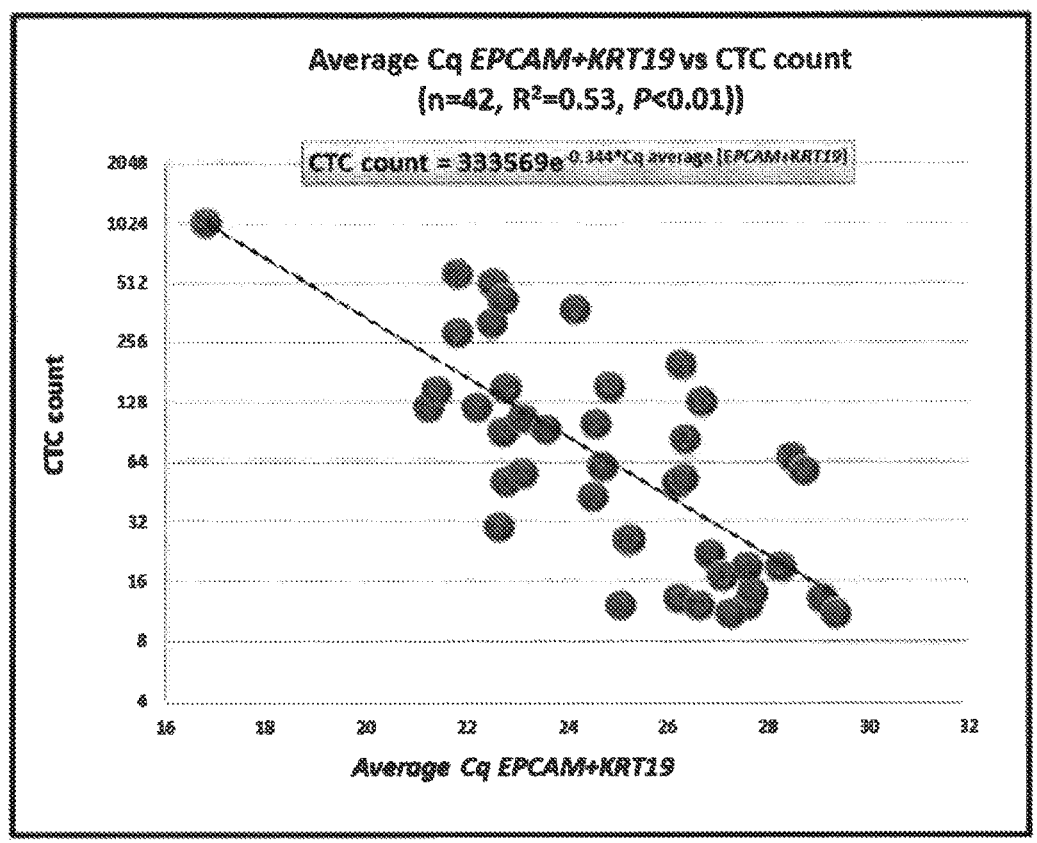
FIG. 4. Sensitivity and specificity of the assays. (A.): Material from 40 mCRPC patients was used to evaluate the linear correlation between CTC count after CellSearch enrichment and the average $C_q$ value of EPCAM and KRT19 in corresponding RNA samples. (B.). Data from 62 individual experiments with input of RNA from 4 to 580 VCAP cells in the RT-qPCR was used to evaluate the linear correlation between the $C_q$ value of AR-V7 and the average $C_q$ value of EPCAM+KRT19. Samples with an average $C_q$ value of EPCAM+KRT19 below 26.5 $C_q$ were considered to contain sufficient epithelial signal to allow measurement of AR-V7 in these cells. Circles: unspiked VCAP cells; squares: VCAP cells spiked in HBD blood. (C.). Sensitivity and specificity measuring AR-WT and AR-V7 by RT-qPCR in VCAP cells before and after spiking in HBD, before and after CellSearch enrichment and before and after pre-amplification. Data are expressed relative to the average expression of EPCAM+KRT19 ($\Delta C_q$) measured in these preparations. Within a window of ±1.1 Cq, both transcripts can be reproducibly measured in material from as little as 2 VCAP cells. Dark blue circles: $\Delta C_q$ AR-WT; squares; light blue circles: $\Delta C_q$ AR-V7.
FIG. 4C is split in two parts wherein the 15 columns that indicate initial cell density are corresponding between the two parts of the figure. In the second part of FIG. 4C, the first 11 cells in row 4 (pre-amplified) indicate "yes", and the remaining 4 cells indicate "no". In the second part of FIG. 4C, the first 4 cells in row 5 (WBC Present) indicate "yes", and the remaining 11 cells indicate "no".

Three reference genes (GUSB, HMBS, and HPRT1) served as internal control of isolated mRNA and cDNA quantity and quality. To estimate the final number of epithelial cells present in our RNA preparations, we used the average signal of EPCAM and KRT19, which correlated with CTC count assessed by CellSearch (Pearson r=0.71; $P<0.01$; FIG. 4A). Final epithelial tumor cell input in the aliquot of RNA used for profiling was then calculated using the equation derived from the regression line of the correlation plot and taking into account that only 11% of the original sample was used. Samples with an average reference gene $C_q$ value >26.5, indicative for low and/or poor RNA/cDNA quality, and/or an average epithelial gene $C_q$ value >26.5, indicative for low/no epithelial CTC input in the final RNA/cDNA sample, were excluded from the analyses.

To correct for CTC count and epithelial tumor cell input, $C_q$ values of AR-V7 and AR-WT were normalized to the average $C_q$ value of the epithelial genes EPCAM and KRT19 measured in the same PCR plate as follows: $\Delta C_q AR$=average $C_q$ value of EPCAM and KRT19 minus $C_q$ value of AR-V7 or AR-WT.

Sensitivity and specificity of the assays were tested through analysis of five healthy blood donors (HBD), and prostate (22RV1, LNCaP, PC3, and VCaP) and breast (CAMA1, MDA-MB-415, MDA-MB-453, MPE600, SUM185PE, and ZR75.1) cancer cell lines. For this purpose, 100 cells of the following cell lines were spiked in 7.5 mL HBD blood and CellSearch-enriched to serve as negative and positive controls: 22RV1 ($WT_{high}/V7_{neg}$), CAMA1 ($WT_{high}/V7_{neg}$), LNCaP ($WT_{high}/V7_{low}$), MDA-MB-415 ($WT_{high}/V7_{neg}$), MDA-MB-453 ($WT_{high}/V7_{neg}$), MPE600 ($WT_{low}/V7_{neg}$), PC3 ($WT_{neg}/V7_{neg}$), SUM185PE ($WT_{high}/V7_{low}$), VCaP ($WT_{high}/V7_{high}$), ZR75.1 ($WT_{low}/V7_{low}$). All samples were processed similarly to the patient blood samples.

Normalization and Statistical Analysis

Three reference genes (GUSB, HMBS, and HPRT1) served as internal control of isolated mRNA quantity and quality. To correct for CTC count and epithelial tumor cell input, $C_q$ values of AR-V7 and AR-WT were normalized to the average $C_q$ value of the epithelial genes EPCAM and KRT19, which correlated with the CTC count (FIG. 4A). Final epithelial tumor cell input in the aliquot of RNA used for profiling was calculated using the equation derived from the regression line of the correlation between the epithelial genes and the CTC count, thereby taking into account that only 11% of the original sample was used. Samples with an average reference gene $C_q$ value >26.5, indicative for low and/or poor RNA quality, and/or an average epithelial gene $C_q$ value >26.5, indicative for low/no epithelial CTC input in the final RNA sample, were excluded from the final clinical analyses. A cut-off value for positivity for AR-V7 was determined based on the cell line experiments (Table 2).

Primary endpoint of this study was the CTC response rate (RR) to cabazitaxel, defined as a decrease from ≥10 CTC to <5/7.5 ml of blood after two treatment cycles. Secondary objectives were PSA response (30% or 50% decline in PSA from baseline to 12 weeks or earlier in case of treatment discontinuation), best PSA response during treatment, and OS (interval between registration and death or last date known alive). Reported endpoints are according to the Prostate Cancer Working Group 2 (PCWG2) guidelines (Scher et al., 2008. J Clin Oncol 26:1148-59).

Applied statistical tests were the $X^2$ test for differences between categorical variables, the Student's t test for normally distributed and the Mann-Whitney U test for other continuous variables. Correlations were tested by Pearson or the non-parametric Spearman's test, depending on the distribution. Survival was visualized using Kaplan Meier plots and differences were calculated through Log-rank testing. All statistical tests were two-sided. A P-value <0.05 was considered statistically significant.

Results

AR-WT and AR-V7 in CTCs

Figure 4B:
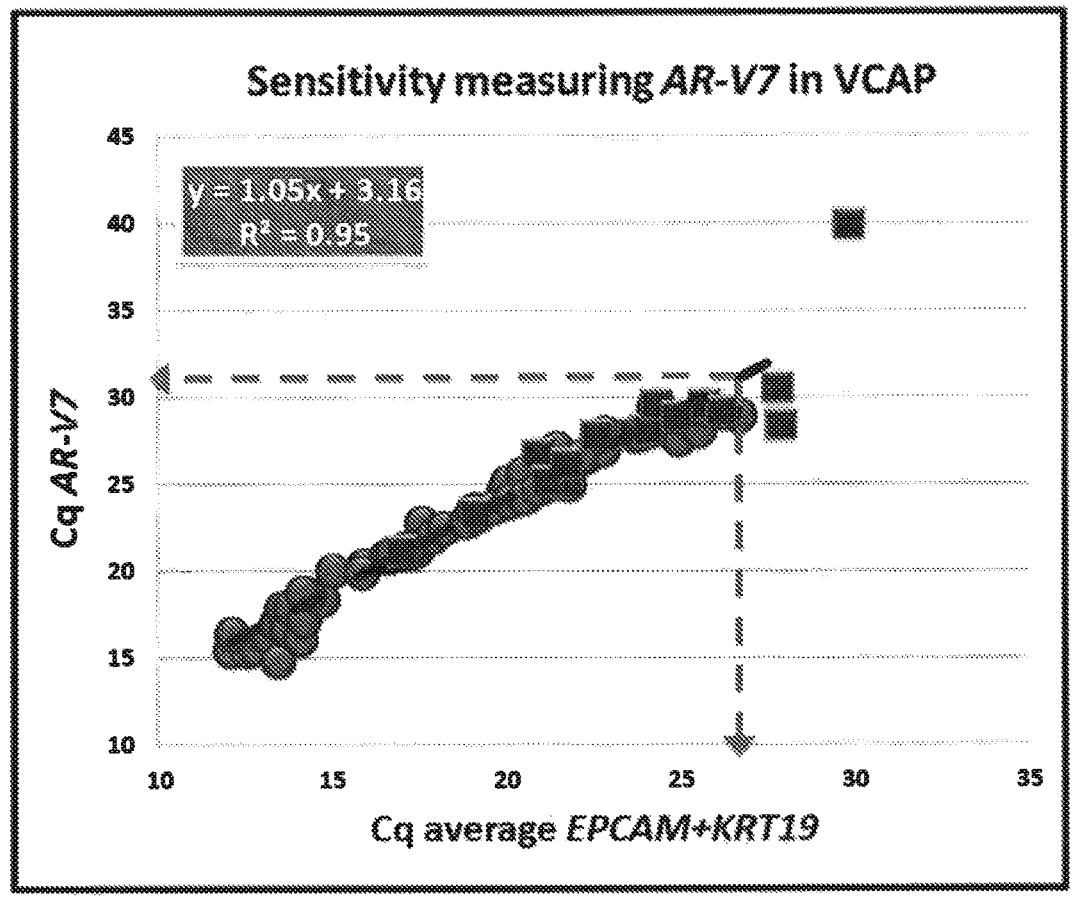
Figure 4C:
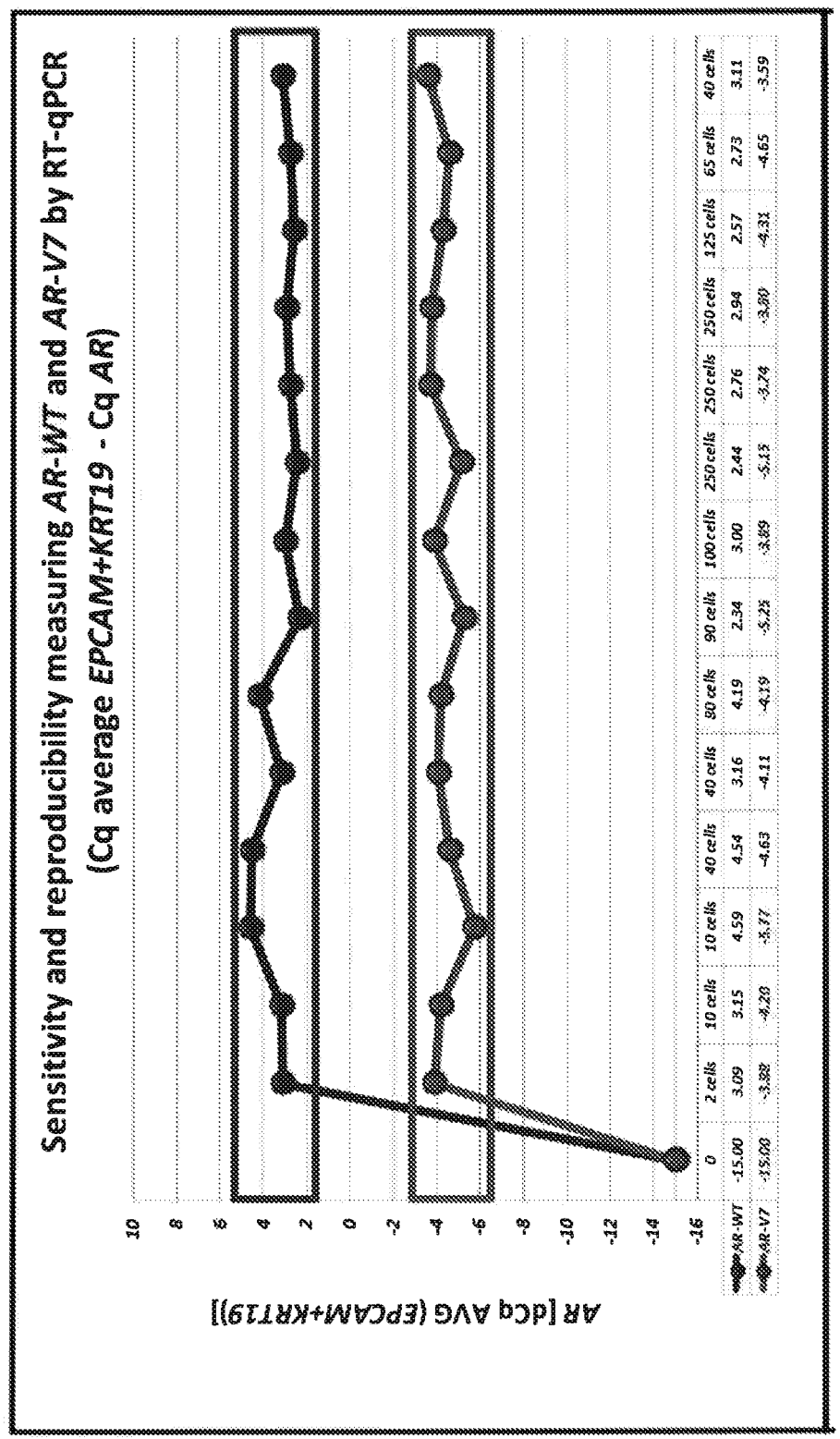

We first tested the sensitivity and specificity of our assays. The average signal of EPCAM and KRT19 correlated with the CTC count as assessed by CellSearch (Pearson r=0.71; P<0.01; FIG. 4A) and was used to estimate the final number of epithelial cells present in our RNA aliquots. To correct for differences in epithelial input between patients, the AR-status was evaluated relative to the expression of the average signal of EPCAM and KRT19. Comparing RNA fractions isolated from pure and spiked-in (100 cells in 7.5 mL HBD blood) breast and prostate cancer cell line cells followed by CellSearch enrichment, we were able to determine the AR-V7 status by RT-qPCR in material isolated from ≥3 spiked-in epithelial cells. This cut-off was confirmed in our clinical samples, where two patients with RNA from 3 CTCs were positive for AR-V7 but none of the patients with <3 CTCs showed a positive AR-V7 signal (Table 2). The leukocyte background did not influence the outcomes of our analyses as the expression levels of AR-WT and AR-V7 before and after spiking and before and after CellSearch enrichment showed strongly correlated (FIG. 4B/C). The lower detection limit of our AR-V7 assay was therefore set at ≥3 epithelial CTCs in the final preparation available for RT-qPCR. Five male HBDs were tested, of whom four were negative for the expression of AR-WT and AR-V7 (Table 2). One 67-year male old HBD had detectable AR-WT in the peripheral blood. Since this donor was anonymous, no follow-up or further diagnostics were done.

Next, patient samples were tested. For this exploratory study, we selected patients with ≥10 CTCs at baseline to limit stochastic variations between the CTC enumeration and isolation assuring epithelial input in the RT-qPCR analyses. Twenty-nine patients with sufficient RNA quality and quantity in the CTC samples were identified (FIG. 1). Patient characteristics are shown in Table 3.

TABLE 3

Patient characteristics in all patients, AR-V7-negative patients, and AR-V7-positive patients.

| | All patients | | AR-V7 in CTCs at baseline | | | | P-value* |
|---|---|---|---|---|---|---|---|
| | | | Absent | | Present | | |
| N | 29 | 100% | 13 | 100% | 16 | 100% | |
| Age at registration (mean ± sd) | 70 ± 7.2 | | 68 ± 8.9 | | 71 ± 5.5 | | 0.30 |
| WHO performance score | | | | | | | 0.27 |
| 0 | 9 | 31% | 6 | 46% | 3 | 19% | |
| 1 | 16 | 55% | 7 | 54% | 9 | 56% | |
| Unknown | 4 | 14% | — | | 4 | 25% | |
| Type of castration | | | | | | | 0.49 |
| Surgical | 3 | 10% | 1 | 8% | 2 | 13% | |
| LHRH agonist | 22 | 76% | 12 | 92% | 10 | 62% | |
| Unknown | 4 | 14% | — | | 4 | 25% | |
| Number of prior chemotherapy lines | | | | | | | 0.90 |
| One (docetaxel) | 22 | 76% | 12 | 92% | 10 | 63% | |
| Two | 2 | 7% | 1 | 8% | 1 | 6% | |
| Unknown | 5 | 17% | — | | 5 | 31% | |
| Prior antiandrogens for mCRPC | | | | | | | |
| Abiraterone acetate | 5 | 17% | 0 | 0% | 5 | 31% | 0.009 |
| Orteronel | 3 | 10% | 3 | 23% | 0 | 0% | 0.09 |
| Baseline chemistry | | | | | | | |
| Lactate dehydrogenase (U/L, median (IQR))*,†† | 460 (325-651) | | 431 (310-616) | | 467 (351-68) | | 0.49 |
| Alkaline phosphatase (U/L, median (IQR))*,†† | 162 (100-382) | | 160 (96-358) | | 270 (100-387) | | 0.08 |
| Prostate specific antigen (µg/L, median (IQR))*,†† | 347 (75-700) | | 107 (68-439) | | 698 (79-952) | | 0.04 |
| Baseline CTC count (median (IQR)) | 100 (50-243) | | 94 (38-260) | | 110 (52-254) | | 0.58 |

Reported P-values are from independent samples Student's t test (age), non-parametric Mann-Whitney U test (baseline chemistry and CTC count), and $\chi^2$ tests (categorical variables).
IQR: interquartile range; sd: standard deviation.
*Missing values are excluded from the analysis.
†Three patients missing, all three AR-V7-positive.
††Upper limit of normal: lactate dehydrogenase: 247 U/L; alkaline phosphatase 114 U/L; prostate specific antigen 6.4 µg/L.

Figure 5:
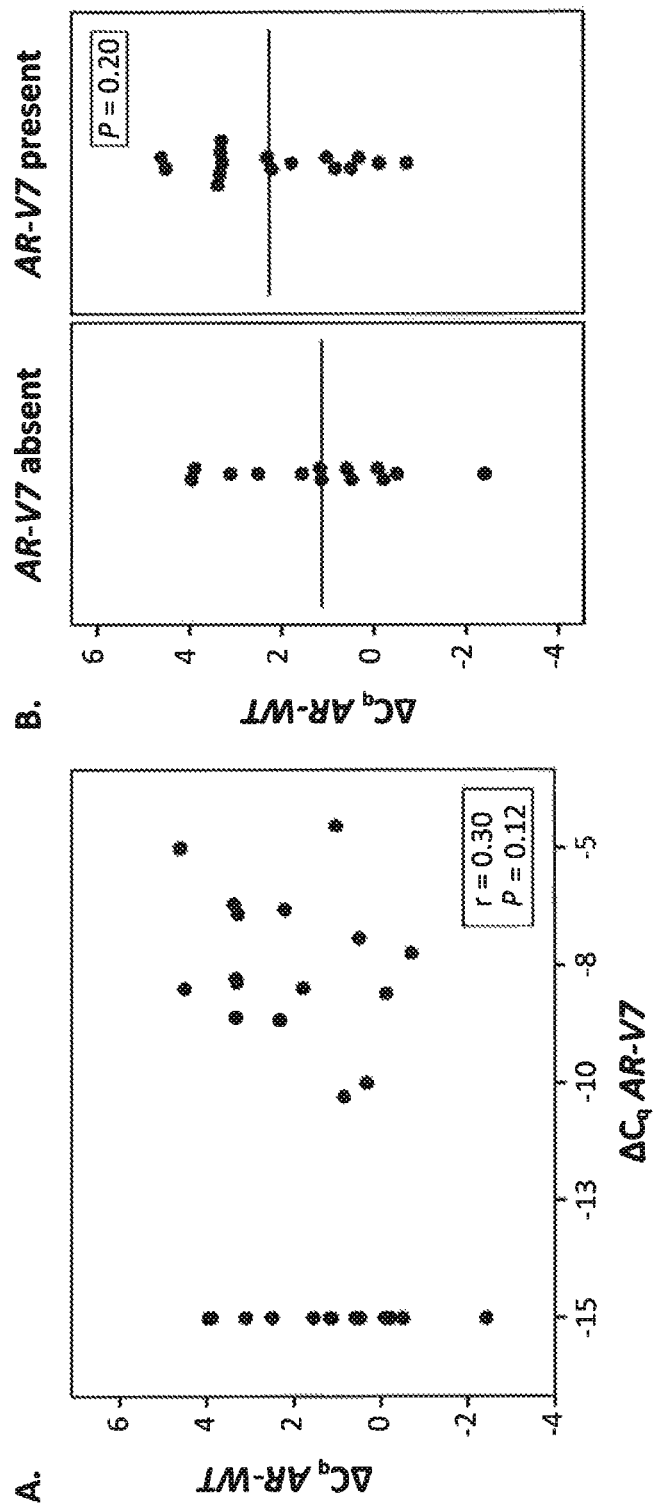
FIG. 5.(A.). Transcription levels of AR-WT versus AR-V7. No correlation was observed (Spearman's r=0.30, P=0.12). (B.). Transcription levels of AR-WT in patients without AR-V7 (left panel) and with AR-V7 (right panel) in CTCs. Horizontal lines represent the medians. There was no difference in transcription levels (Mann Whitney U, P=0.20).

Five patients had received abiraterone acetate before enrollment. Expression of AR-WT in CTCs was detected in all patients. In 16 patients (55%) expression of AR-V7 was measured. All five patients who had previously been treated with abiraterone acetate expressed AR-V7 compared to seven of the 20 patients (35%) who had not received abiraterone acetate (P=0.009). Patients with AR-V7-positive CTCs had higher median PSA levels than did AR-V7-negative patients (698 versus 107 µg/L; P=0.04). Expression levels of AR-V7 in CTCs were not correlated to AR-WT expression levels (Spearman's r=0.30, P=0.12; FIG. 5A). There was no difference in AR-WT expression levels between patients with and without AR-V7 in the CTCs (P=0.20; FIG. 5B).

AR-V7 and Response to Cabazitaxel

Primary endpoint of this study was the CTC response after two cabazitaxel cycles, defined as a decrease from ≥10 CTCs at baseline to <5 CTCs/7.5 mL of blood after two cycles. From 25 patients a secondary CTC sample was available; in three patients the second draw was missed and one patient died after the second cycle because of a non-disease related event. Of these 25 patients, 15 were AR-V7-positive and 10 were AR-V7-negative. A CTC response to cabazitaxel was observed in five of the 25 patients (20%), three of whom expressed AR-V7 in the baseline CTCs. The CTC-RRs in both AR-V7-positive and AR-V7-negative patient groups were 20% (Table 4).

TABLE 4

Presence of AR-V7 in CTCs at baseline versus CTC response to cabazitaxel after two cycles, PSA response after 12 weeks, and best PSA response at the end of treatment.

|  |  | CTC response | | PSA response after 12 weeks | | | Best PSA response | | |
|---|---|---|---|---|---|---|---|---|---|
|  |  | No | Yes | No | ≥30%* | ≥50% | No | ≥30%* | ≥50% |
| AR-V7 | No | 8 | 2 | 9 | 3 | 2 | 7 | 4 | 2 |
| AR-V7 | Yes | 12 | 3 | 12 | 2 | 1 | 12 | 3 | 1 |

*Numbers include patients with ≥50% PSA response.
$X^2$ P = 1.00
$X^2$ P = 0.74
$X^2$ P = 0.59

Figure 2A:
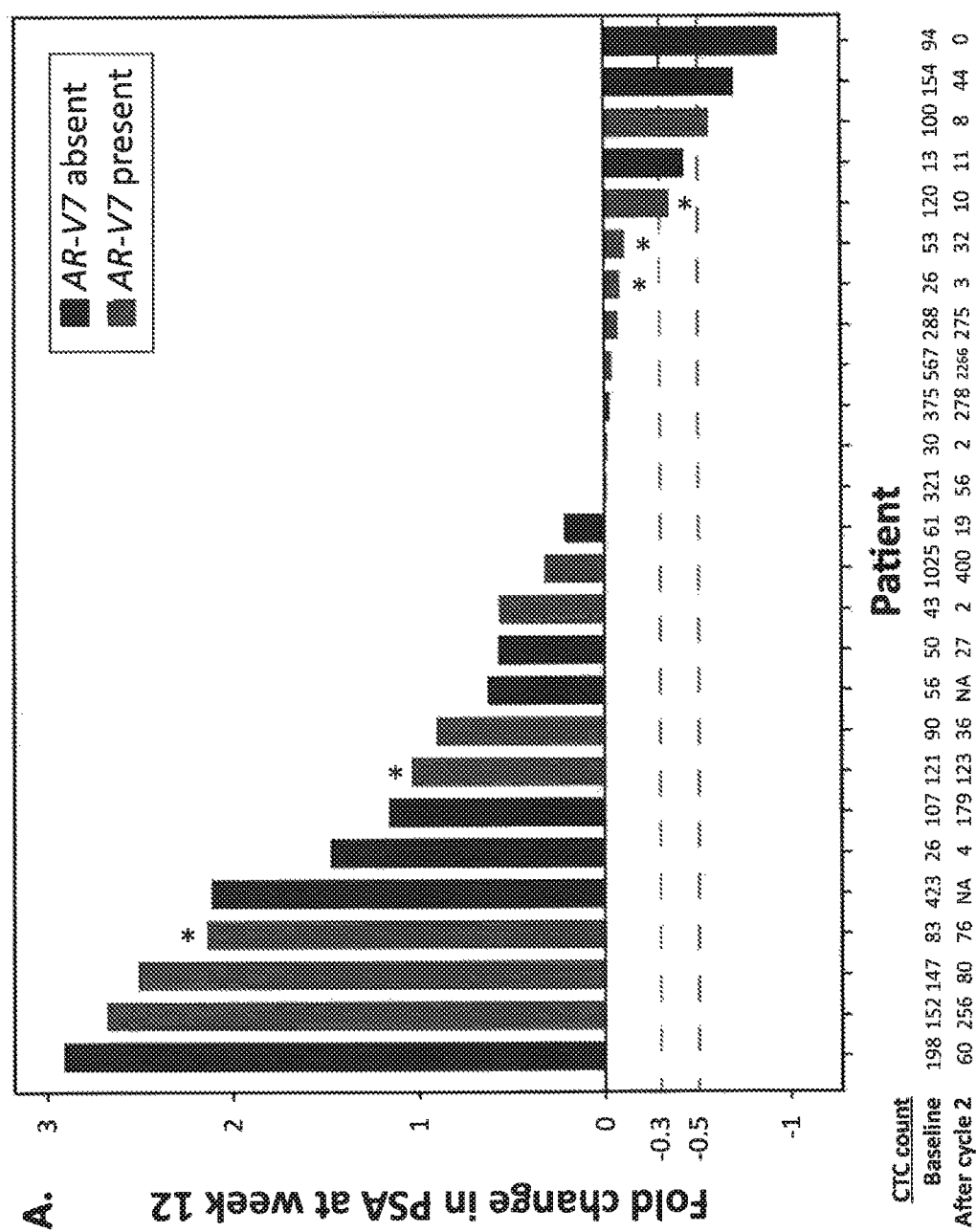
FIG. 2. Waterfall plots of PSA responses to cabazitaxel after 12 weeks (A.) and at the end of treatment (B.). The dashed lines represent 30% and 50% decreases in PSA relative to the baseline level. No differences in PSA responses were observed between AR-V7-positive and AR-V7-negative patients. Asterisks above or below the columns indicate patients that were treated with abiraterone acetate before cabazitaxel.
Figure 2B:
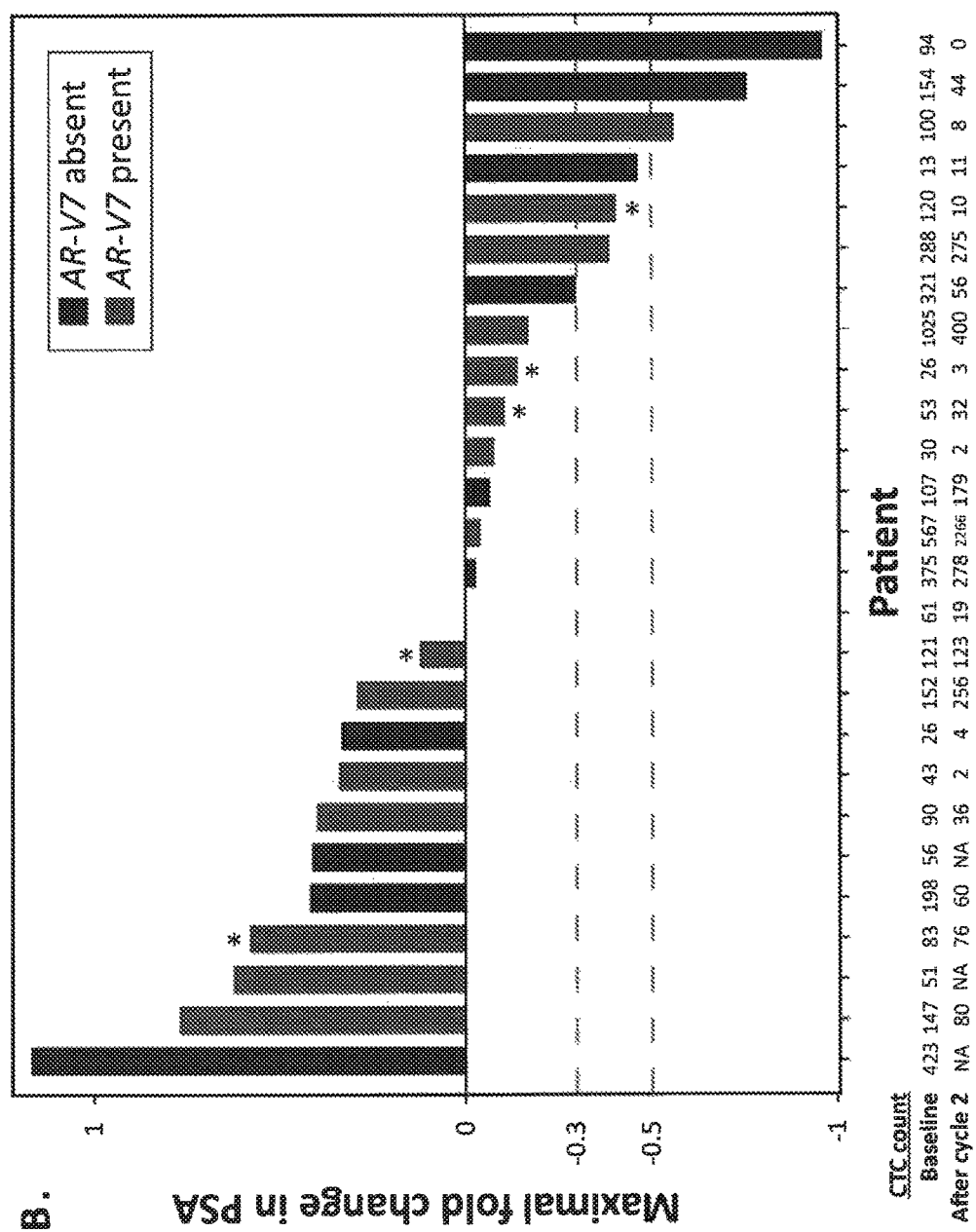

Sequential PSA levels during cabazitaxel for evaluation of PSA response after 12 weeks and maximal PSA response at the end of treatment were available from 26 patients. Five (17%) and three patients (10%) achieved a ≥30% and ≥50% PSA response, respectively, after 12 weeks of treatment. At the end of treatment, the best PSA response was ≥30% in seven patients (24%) and ≥50% in three patients (10%). The differences between 30% and 50% PSA-RR after 12 weeks and at the end of treatment between patients with and without AR-V7 in CTCs were not statistically significant (Table 4, FIG. 2). Prior abiraterone acetate treatment had no influence on CTC-RR and PSA-RR during cabazitaxel treatment.

AR-V7 and Survival

Figure 3:
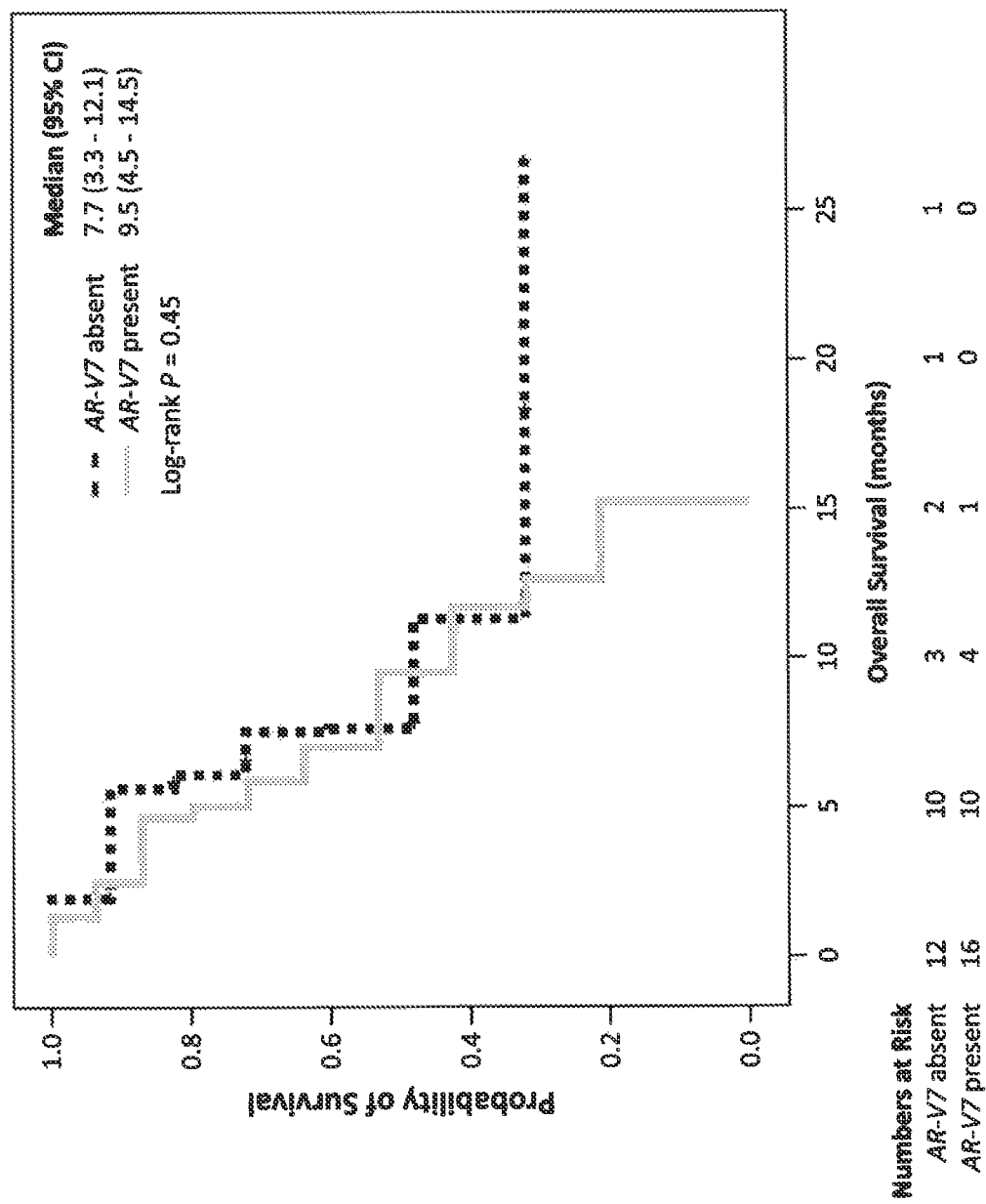
FIG. 3. Overall survival as a function of AR-V7 in CTCs at baseline. The reported P-value is from Log-rank testing. Follow-up data from three patients were still missing at the time of the analyses as the clinical trial was still ongoing and recruiting.
Figure 6A:
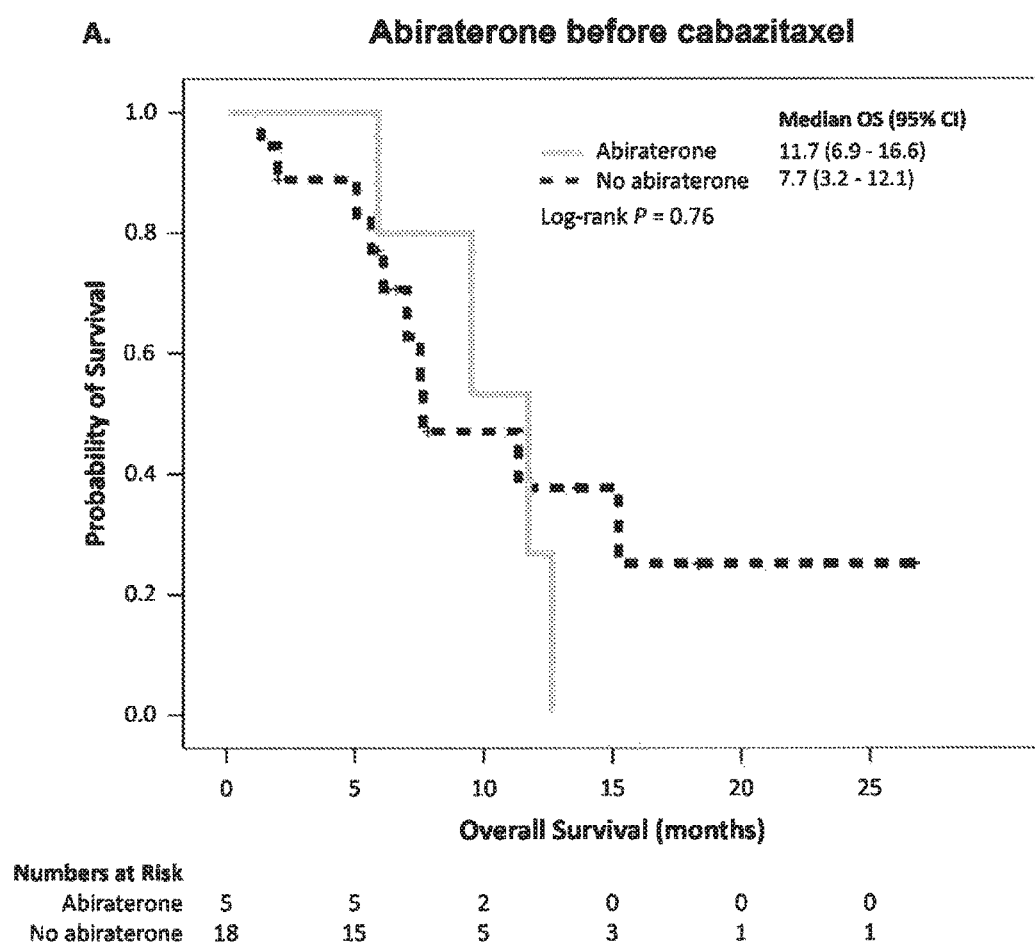
FIG. 6. Overall survival in patients that did or did not receive abiraterone acetate before cabazitaxel (A.) and patients that did or did not receive abiraterone acetate or enzalutamide after cabazitaxel (B.). Clinical data concerning pre-treatments of five patients were still missing as the clinical trial was still ongoing and recruiting. From one patient no follow-up data was yet available.
Figure 6B:
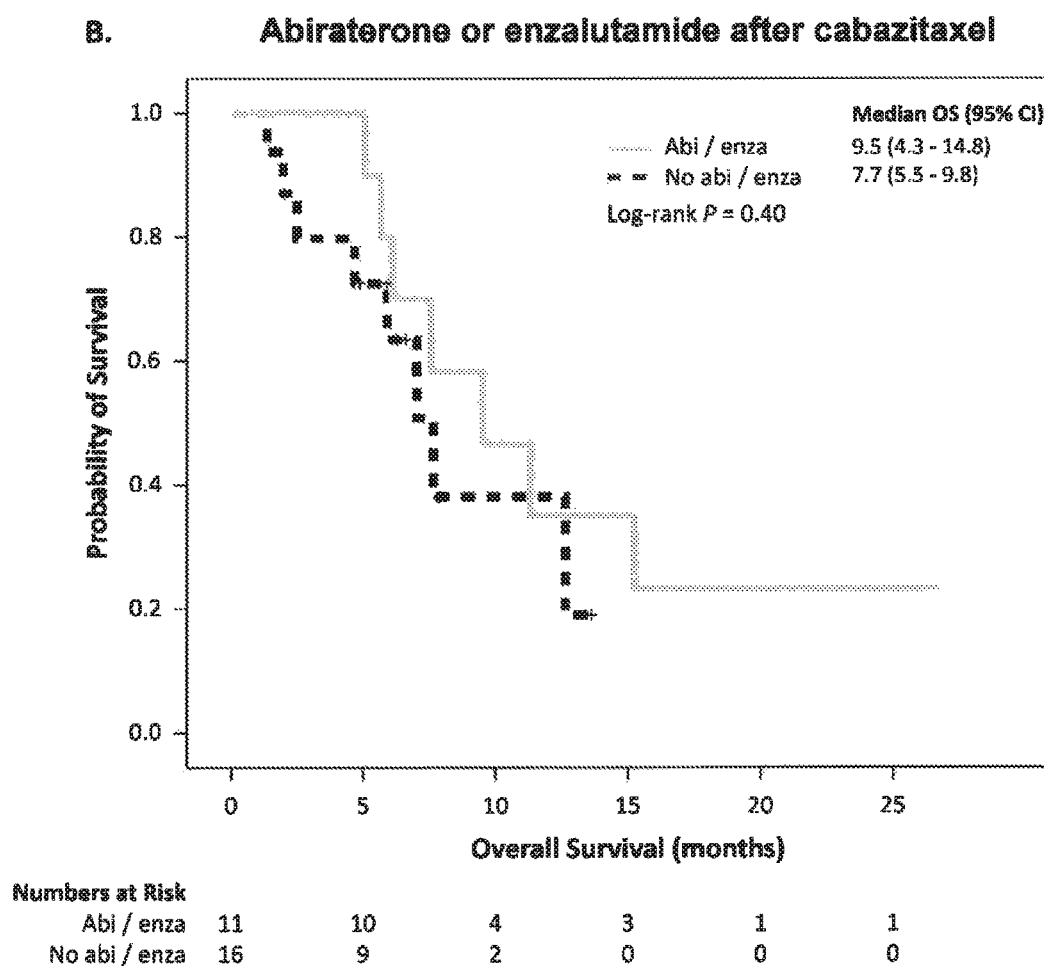

Twenty-eight patients were available for the OS analysis. Median follow-up time from the date of registration for the 12 patients still alive was 6.6 months (range 1.7-26.7 months). Four patients were still receiving cabazitaxel treatment. Median OS in all patients was 9.5 (95% CI 5.8-13.2) months. Presence of AR-V7 in CTCs at baseline was not associated with OS (FIG. 3). Median OS in patients with AR-V7 was 9.5 (95% CI 4.5-14.5) months compared to 7.7 (95% CI 3.3-12.1) months in patients without AR-V7 (Log-rank P=0.45). Treatment with abiraterone acetate before or after cabazitaxel had no influence on OS (FIG. 6).

It is shown herein that repetitive analysis of molecular characteristics of (circulating) tumor cells during the treatment trajectory may be very beneficial for personalized treatments as tumor characteristics can change over time and these changes may impact outcome to systemic treatments. Characterization of CTCs provides a minimally invasive way to monitor changes in characteristics of metastatic tumor sites, potentially including intra- and intertumoral lesion heterogeneity. However, advanced and extremely sensitive methods are needed for the isolation and characterization of CTCs, given their low numbers in the circulation. Among the numerous isolation assays developed, the CellSearch System is the only FDA-certified for clinical use. No CTC characterization assay has been validated so far.

Nevertheless, the feasibility and clinical relevance of measuring AR-V7 in CTCs of mCRPC patients treated with enzalutamide or abiraterone acetate has recently been shown (Antonarakis et al. 2014). In this study, CTCs were enriched from peripheral blood using an mRNA-based isolation method, for which limited data exist concerning the clinical relevance in mCRPC. In the present study, we explored the feasibility to measure AR-WT and AR-V7 in CTCs after enrichment from peripheral blood by the CellSearch assay. Based on spiking experiments using cancer cell lines, we were able to reliably detect AR-V7 in ≥3 CTCs in 7.5 mL blood. A cut-off for AR-V7 positivity was established based on the cell line experiments and applied to patient samples. Differences in epithelial input were corrected through normalization using the epithelial markers that strongly correlated with CTC count. Altogether, we describe a robust method to measure AR-WT and AR-V7 in CTCs isolated using the CellSearch System.

Given the recently described predictive role of AR-V7 for resistance to abiraterone acetate, enzalutamide, and docetaxel, we subsequently assessed the association between AR-V7 presence in CTCs and outcome to cabazitaxel. In contrast to docetaxel, for which cross-resistance with abiraterone acetate and enzalutamide has been described, patients failing to before-mentioned treatments still seem to benefit from cabazitaxel. In our cohort of docetaxel pre-treated mCRPC patients with ≥10 CTCs, we detected AR-V7 in 16 of the 29 (55%) patients, which is higher than the earlier found 29% of enzalutamide and abiraterone acetate treated patients, of whom 40% had been treated with docetaxel. The higher prevalence of AR-V7 in our study might reflect the overall poorer prognosis of our patient group compared to the prior study group, where also patients with <10 CTCs were included. Consistent with the earlier study, the prevalence of AR-V7 was significantly higher in abiraterone acetate-resistant patients. Presence of AR-V7 was found to predict resistance to abiraterone acetate and enzalutamide (Antonarakis et al. 2014). We herein show that the presence of AR-V7 in CTCs taken prior to treatment was not associated with outcome to cabazitaxel with CTC-RRs of 20% both in patients with and without AR-V7. Also in contrast to the findings in enzalutamide- and abiraterone acetate-treated patients, OS after cabazitaxel treatment was not associated with the presence of AR-V7 in CTCs. Our results indicate that cabazitaxel still is a valid treatment option for AR-V7-positive patients.

We chose to use the CTC-RR—defined as a decrease in CTC count to <5/7.5 mL blood after two cabazitaxel cycles—as main endpoint for treatment efficacy. The robustness of this endpoint was established in several prior studies showing that CTC numbers are strongly associated with PFS and OS in mCRPC patients and that patients with a high baseline CTC count of ≥5 CTCs but a decline to <5 per 7.5 ml of blood fare better than patients who remained at a high CTC number. In addition, the combination of CTC count and lactate dehydrogenase (LDH) levels showed to fulfill all criteria for survival surrogacy, supporting the use of CTCs as surrogate endpoint for OS in clinical trials. Since it is still widely used, we also analyzed the PSA-RR as secondary endpoint. No differences were observed between AR-V7-positive and AR-V7-negative patients and PSA response after 12 weeks and at the end of treatment.

The lack of predictive value of AR-V7 in baseline CTCs for response to cabazitaxel is novel and surprising and cabazitaxel is indicated as a valid treatment option for AR-V7-positive patients, possibly even for patients with fewer CTCs than the current limit of detection of AR-V7 in samples containing ≥3 epithelial CTCs.

In conclusion, we here demonstrated the feasibility to measure AR-V7 in CTCs after CellSearch enrichment in mCRPC patients. We showed that outcome to cabazitaxel in these patients is not associated with the presence of this particular splice variant. These results add important information to the existing evidence that CTCs provide an invaluable tool to personalize cancer treatments and improve the prognosis of mCRPC patients by allowing optimal treatment sequencing.

The invention claimed is:

1. A method of treating a patient suffering from prostate cancer comprising determining the androgen receptor mRNA splice variant 7 (AR-V7)-status in said patient and administering a therapeutically effective amount of cabazitaxel in base form or in the form of an hydrate or a solvate, to an AR-V7-positive patient, in combination with a corticoid.

2. The method of claim 1, wherein said prostate cancer is metastatic castration-resistant prostate cancer.

3. The method of claim 1, wherein said corticoid is prednisone or prednisolone.

4. The method of claim 1, wherein said step of determining the AR-V7-status in said patient is performed on isolated tumor cells.

5. The method of claim 1, wherein said step of determining the AR-V7-status in said patient is performed on isolated circulating tumor cells (CTCs).

6. The method of claim 1, wherein said patient has been previously treated with a docetaxel-based regimen.

7. The method of claim 1, wherein said patient is resistant to docetaxel.

8. The method of claim 1, wherein said patient has been previously treated with and/or is resistant to abiraterone acetate and/or enzalutamide.

9. The method of claim 1, wherein said cabazitaxel is in the form of an acetone solvate.

10. The method of claim 9, in which the acetone solvate contains between 5% and 8% by weight of cabazitaxel.

11. The method of claim 3, wherein said cabazitaxel is administered at a dose of between 15 and 25 mg/m2, the prednisone or prednisolone being administered at a dose of 10 mg/day.

12. The method of claim 11, wherein said cabazitaxel is administered at a dose of 25 mg/m2.

13. The method of claim 1, comprising repeating the administration of cabazitaxel as a new cycle every 3 weeks.

14. The method of claim 13, wherein the median number of cycles is 6.

15. The method of claim 1, further comprising testing the AR-V7-status of circulating tumor cells in a biological sample from the patient, and administering a therapeutically effective amount of cabazitaxel in base form or in the form of an hydrate or a solvate, in combination with a corticoid to the patient if the sample tests positive for AR-V7.

16. The method of claim 15, wherein said method comprises the steps of:
(a) determining the AR-V7-status in isolated tumor cells, in one of a blood, serum or urine sample obtained from the patient, said step of determining comprising:
magnetically separating said tumor cells from essentially all other cells in the sample using ferrofluid nanoparticles with antibodies that target epithelial cell adhesion, to provide an enriched tumor cells sample;
optionally enumerating said isolated tumor cells in said enriched tumor cells sample by staining said tumor cells in said sample with a nuclear DNA stain, and a cytokeratin monoclonal antibody specific to epithelial cells, while optionally differentiating said dual stained tumor cells from stained leukocytes in said sample using a leukocyte-specific anti-CD45 monoclonal antibody stain, and
determining the presence of androgen receptor mRNA splice variant 7 transcripts in tumor cells in said enriched tumor cells sample by reverse transcription quantitative polymerase chain reaction (RT-qPCR), whereby the presence of AR-V7 transcripts in said tumor cells indicates an AR-V7-positive status of said patient; and
(b) treating the prostate cancer in the patient in case said patient has an AR-V7-positive status comprising administering to said patient a therapeutically effective amount of cabazitaxel in base form or in the form of an hydrate or a solvate, in combination with a corticoid.

17. The method of claim 1, wherein determining the AR-V7 status of said patient comprises testing a biological sample from the patient for the presence of AR-V7 circulating tumor cells, wherein the patient is eligible for treatment with said cabazitaxel if circulating tumor cells in said sample test positive for AR-V7.

18. The method of claim 17, wherein said step of testing a biological sample from the patient for the presence of AR-V7 circulating tumor cells comprises:
(a) providing one of a blood, serum or urine sample from the patient,
(b) magnetically separating said tumor cells from essentially all other cells in said sample using ferrofluid nanoparticles with antibodies that target epithelial cell adhesion, to provide an enriched tumor cells sample;
(c) optionally enumerating said isolated tumor cells in said enriched tumor cells sample by staining said tumor cells in said sample with a nuclear DNA stain, and a cytokeratin monoclonal antibody specific to epithelial cells, while optionally differentiating said dual stained tumor cells from stained leukocytes in said sample using a leukocyte-specific anti-CD45 monoclonal antibody stain, and
(d) determining the presence of androgen receptor mRNA splice variant 7 transcripts in tumor cells in said enriched tumor cells sample by reverse transcription quantitative polymerase chain reaction (RT-qPCR).

19. The method of claim 1, wherein determining the AR-V7 status of said patient comprises using a kit comprising primers for amplifying androgen receptor mRNA splice variant 7 transcripts in tumor cells by reverse transcription quantitative polymerase chain reaction (RT-qPCR), and further comprising ferrofluid nanoparticles with antibodies that target epithelial cell adhesion, for enriching tumor cells from essentially all other cells in the patient sample by magnetic separation, optionally in combination with instructions for determining the eligibility of the patient with prostate cancer to treatment with cabazitaxel based on the diagnostic test result results for the AR-V7-status obtained, and/or instructions for treating said patient with cabazitaxel.

* * * * *